US009568449B2

(12) United States Patent
Downey et al.

(10) Patent No.: US 9,568,449 B2
(45) Date of Patent: Feb. 14, 2017

(54) DIELECTRIC SPECTROSCOPY METHODS AND APPARATUS

(71) Applicant: Bend Research, Inc., Bend, OR (US)

(72) Inventors: Brandon J. Downey, Bend, OR (US); Jeffery F. Breit, Bend, OR (US); Lisa Graham, Bend, OR (US); Adam S. Carroll, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

(21) Appl. No.: 14/370,734

(22) PCT Filed: Jan. 4, 2013

(86) PCT No.: PCT/US2013/020397
§ 371 (c)(1),
(2) Date: Jul. 3, 2014

(87) PCT Pub. No.: WO2013/103901
PCT Pub. Date: Jul. 11, 2013

(65) Prior Publication Data
US 2015/0019140 A1 Jan. 15, 2015

Related U.S. Application Data

(60) Provisional application No. 61/703,103, filed on Sep. 19, 2012, provisional application No. 61/699,805, filed on Sep. 11, 2012, provisional application No. 61/584,141, filed on Jan. 6, 2012.

(51) Int. Cl.
*G01N 27/22* (2006.01)
*C12M 1/34* (2006.01)
*G01N 33/483* (2006.01)

(52) U.S. Cl.
CPC .............. *G01N 27/22* (2013.01); *C12M 41/36* (2013.01); *C12M 41/46* (2013.01); *G01N 27/221* (2013.01); *G01N 33/4833* (2013.01)

(58) Field of Classification Search
None
See application file for complete search history.

(56) References Cited

U.S. PATENT DOCUMENTS

| | | | |
|---|---|---|---|
| 3,713,988 | A | 1/1973 | Dawson et al. |
| 4,810,650 | A | 3/1989 | Kell et al. |
| 4,965,206 | A | 10/1990 | Kell |
| 5,296,197 | A | 3/1994 | Newberg et al. |
| 6,482,619 | B1 | 11/2002 | Rubinsky et al. |
| 6,496,020 | B1 | 12/2002 | Davey et al. |
| 6,596,507 | B2 | 7/2003 | Ossart |
| 7,930,110 | B2 | 4/2011 | Ossart et al. |
| 2008/0312843 | A1 | 12/2008 | Esteban et al. |
| 2010/0236340 | A1 | 9/2010 | Lee et al. |

FOREIGN PATENT DOCUMENTS

| | | |
|---|---|---|
| FR | 2617286 | 12/1988 |
| WO | WO 93/18395 | 9/1993 |
| WO | WO 2006/086489 | 8/2006 |
| WO | WO 2011/038008 | 3/2011 |

OTHER PUBLICATIONS

Ansorge et al., "Multifrequency Permittivity Measurements Enable On-Line Monitoring of Changes in Intracellular Conductivity Due to Nutrient Limitations During Batch Cultivations of CHO Cells," *Biotechnology Progress*, vol. 26, Issue 1, Jan./Feb. 2010, pp. 272-283.
Ansorge et al., "On-line monitoring of infected Sf-9 insect cell cultures by scanning permittivity measurements and comparison with off-line biovolume measurements," *Cytotechnolog*, vol. 55, Issues 2-3, Dec. 2007, pp. 115-124.
Ansorge et al., "On-line monitoring of responses to nutrient feed additions by multi-frequency permittivity measurements in fed-batch cultivations of CHO cells," *Cytotechnology*, vol. 62, Issue 2, Apr. 2010, pp. 121-132.
Asami, "Characterization of heterogeneous systems by dielectric spectroscopy," *Prog. Polym. Sci*, vol. 27, Issue 8, Oct. 1, 2002, pp. 1617-1659.
Asami et al., "Dielectric analysis of yeast cell growth," *Biochim Biophys Acta.*, Aug. 17, 1995, pp. 99-105.
Asami et al., "Dielectric dispersion in biological cells of complex geometry simulated by the three-dimensional finite difference method," *Journal of Physics D: Applied Physics*, vol. 39, No. 3, Jan. 20, 2006, pp. 492-499.
Benz, "Bioreactor Design for Chemical Engineers," *CEP Magazine*, Aug. 2011, pp. 21-26.
Bot et al., "Probing the membrane potential of living cells by dielectric spectroscopy," *Eur Biophys J*, vol. 38, Issue 8, Oct. 2009, pp. 1049-1059.
Dabros et al., "Cole-Cole, linear and multivariate modeling of capacitance data for on-line monitoring of biomass," *Bioprocess and Biosystems Engineering*, vol. 32, No. 2, Jun. 11, 2008, pp. 161-173.

(Continued)

*Primary Examiner* — Lori A. Clow
*Assistant Examiner* — Olivia Wise
(74) *Attorney, Agent, or Firm* — Klarquist Sparkman, LLP

(57) ABSTRACT

Methods and apparatus are disclosed for correcting measurements received by applying a frequency-varying signal with a measuring device (e.g., a permittivity probe) to a population of living cells (e.g., contained in a bioreactor) and correcting measurement divergences using data acquired using an alternate analytical method (e.g., trypan blue exclusion). In one example, a method comprises receiving electrical property data for a first population of cells, the data obtained by applying a first frequency-varying signal to the population with a measuring device, receiving biological property data obtained using an alternate analytical technique, generating at least one value representative of the frequency dependence of the electrical property data, and determining a relationship between the biological property data and the representative value. In some examples, measurements of apoptosis are predicted using the electrical property data.

18 Claims, 28 Drawing Sheets

(56) References Cited

OTHER PUBLICATIONS

Daken Stainless Products: "Keofitt W15 Sample Valves," http://www.keofit-tuk.com/865541.htm, (document downloaded Jul. 3, 2014) 1 page.

Davey et al., "The influence of electrode polarisation on dielectric spectra, with specialreference to capacitive biomass measurements I. Quantifying the effects on electrode polarisation of factors likely to occur during fermentations," *Bioelectrochemistry and Bioenergetics*, vol. 46, Issue 1, Aug. 1988, pp. 91-103.

Di Biasio et al., "D-glucose-induced alterations in the electrical parameters of human erythrocyte cell membrane," *Bioelectrochemistry*, vol. 77, Issue 2, Feb. 2010, pp. 151-157.

Di Biasio et al., "The Dielectric Behavior of Nonspherical Biological Cell Suspensions: an Analytic Approach," *Biophysical Journal*, vol. 99, Jul. 2010, pp. 163-174.

Gheorghiu, "Measuring living cells using dielectric spectroscopy," *Institute of Biotechnology*, vol. 40, Issue 2, Aug. 1996, pp. 133-139.

Heinrich et al., "Utilization of multifrequency permittivity measurements in addition to biomass monitoring," $22^{nd}$ *European Society for Animal Cell Technology (ESACT) Meeting on Cell Based Technologies*, May 2011, 2 pages.

International Search Report for PCT/US2013/020397, mailed Mar. 21, 2013, 4 pages.

Irimajiri et al., "Passive electrical properties of the membrane and cytoplasm of cultured rat basophil leukemia cells," *Biochim Biophysica Acta*, Apr. 23, 1987, pp. 214-223.

Ishikawa et al., "Freezing Injury of Cultured Rice Cells Analyzed by Dielectric Measurement," *Journal of Fermentation and Bioengineering*, vol. 83, No. 3, Jan. 1997, pp. 222-226.

Justice et al., "Process control in cell culture technology using dielectric spectroscopy," *Biotechnology Advances*, vol. 29, Issue 4, Jul.-Aug. 2011, pp. 391-401.

Labeed et al., "Differences in the biophysical properties of membrane and cytoplasm of apoptotic cells revealed using dielectrophoresis," *Biochim Biophys Acta*, vol. 1760, Issue 6, Jun. 2006, pp. 922-929.

Lee et al., "Distinguishing between apoptosis and necrosis using a capacitance sensor," *Biosensors and Bioelectronics*, vol. 24, Issue 8, Apr. 15, 2009, pp. 2586-2591.

Mishima et al., "On-Line Monitoring of Cell Concentrations during Yeast Cultivation by Dielectric Measurements," *Journal of Fermentation and Bioengineering*, vol. 72, No. 4, 1991, pp. 296-299.

Opel et al., "Quantitative modeling of viable cell density, cell size, intracellular conductivity, and membrane capacitance in batch and fed-batch CHO processes using dielectric spectroscopy," *Biotechnology Progress*, vol. 26, No. 4, Jan. 1, 2010, pp. 1187-1199.

Patel et al., "Dielectric measurement of cell death," *Enzyme and Microbial Technology*, vol. 43, Issue 7, Dec. 2008, pp. 463-470.

Perkel, "Cell Counting," *Biocompare Buyer's Guide for Life Scientists*, May 12, 2010, 4 pages.

Pethig et al., "Applications of dielectrophoresis in biotechnology," *Trends in Biotechnology*, vol. 15, Issue 10, Oct. 1997, pp. 426-432.

Polevaya et al., "Time domain dielectric spectroscopy study of human cells II. Normal and malignant white blood cells," *Biochim Biophysica Acta*, vol. 1419, Issue 2, Jul. 1999, pp. 257-271.

Prodan et al., "Correcting the polarization effect in very low frequency dielectric spectroscopy," *J. Phys. D: Appl. Phys.*, vol. 42, No. 17, 2009, 11 pages.

Prodan et al., "The Dielectric Response of Spherical Live Cells in Suspension: an Analytic Solution," *Biophysical Journal*, vol. 95, Nov. 2008, pp. 4174-4182.

Ron et al., Cell-based screening for membranal and cytoplasmatic markers using dielectric spectroscopy, *Biophysical Chemistry*, vol. 135, Issues 1-3, Jun. 2008, pp. 59-68.

Ron et al., "Dielectric dispersion of suspended cells using 3D reconstructed morphology model," *Bioelectrochemistry*, vol. 75, Issue 2, Jun. 2009, pp. 95-103.

Ron et al., "Dielectric screening of early differentiation patterns in mesenchymal stem cells induced by steroid hormones," *Bioelectrochemistry*, vol. 78, Issue 2, Jun. 2010, pp. 161-172.

Ron et al., "The effect of irregularity on the dielectric dispersion characteristics of spherical cellular suspension," *Colloids and Surfaces B: Biointerfaces*, vol. 74, Issue 1, Nov. 2009, pp. 127-135.

Ron et al., "Theoretical examination of aggregation effect on the dielectric characteristics of spherical cellular suspension," *Biophysical Chemistry*, vol. 140, Issues 1-3, Mar. 2009, pp. 39-50.

Soley et al., "On-line monitoring of yeast cell growth by impedance spectroscopy," *Journal of Biotechnology*, vol. 118, No. 4, Sep. 10, 2005, pp. 398-405.

Stoneman et al., "Protein influence on the plasma membrane dielectric properties: in vivo study utilizing dielectric spectroscopy and fluorescence microscopy," *Bioelectrochemistry*, vol. 70, Issue 2, May 2007, pp. 542-550.

Tibayrenc et al., "Online monitoring of dielectrical properties of yeast cells during a stressmodel alcoholic fermentation," *Process Biochemistry*, vol. 46, Issue 1, Jan. 2011, pp. 193-201.

Wang et al., "Membrane dielectric changes indicate induced apoptosis in HL-60 cells more sensitively than surface phosphatidylserine expression or DNA fragmentation," *Biochim Biophys Acta*, vol. 1564, Issue 2, Aug. 31, 2002, pp. 412-420.

Written Opinion of the International Searching Authority for PCT/US2013/020397, mailed Mar. 21, 2013, 4 pages.

Yardley et al., "Correction of the influence of baseline artefacts and electrode polarisation on dielectric spectra," *Bioelectrochemistry*, vol. 51, Issue 1, Feb. 2000, pp. 53-65.

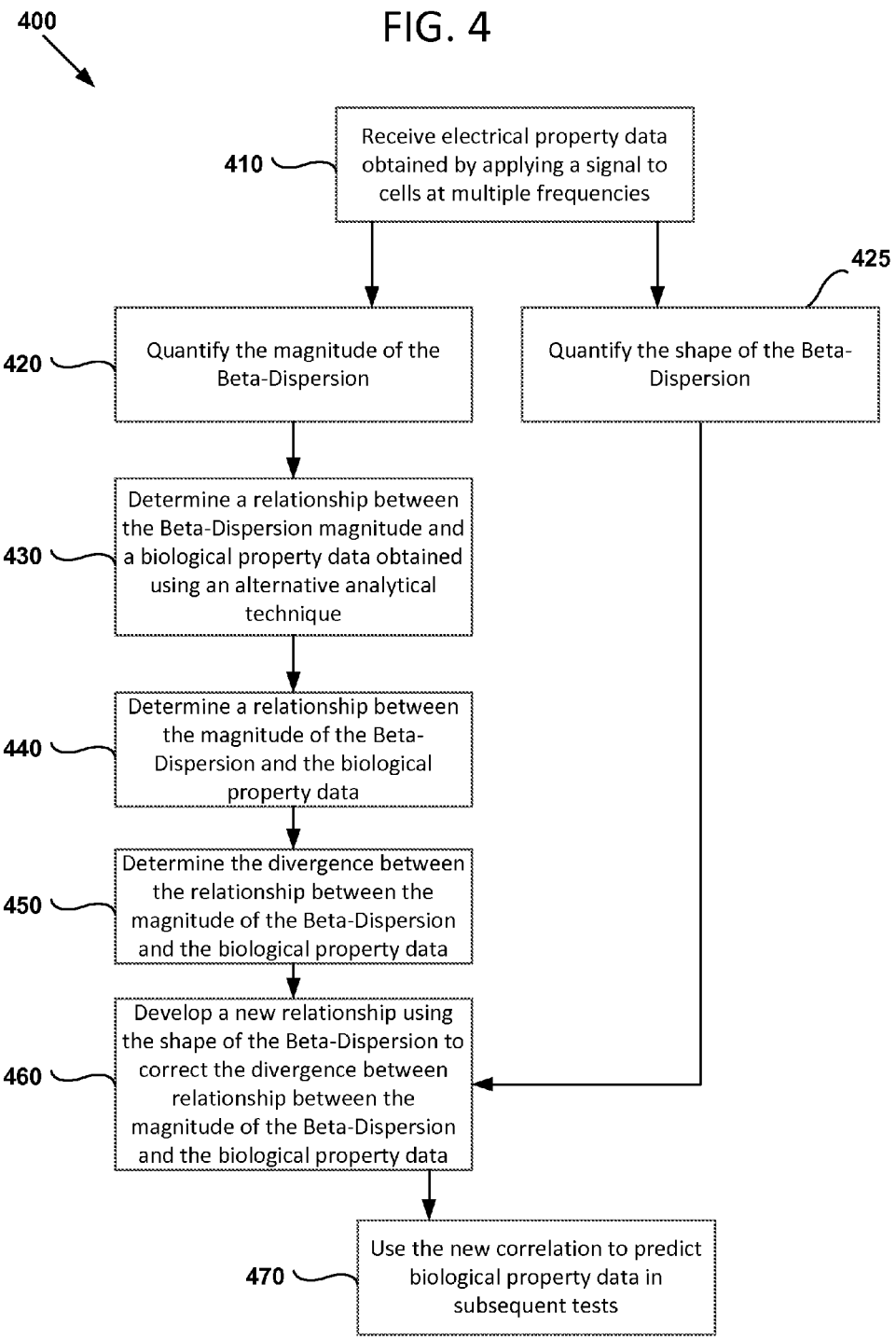

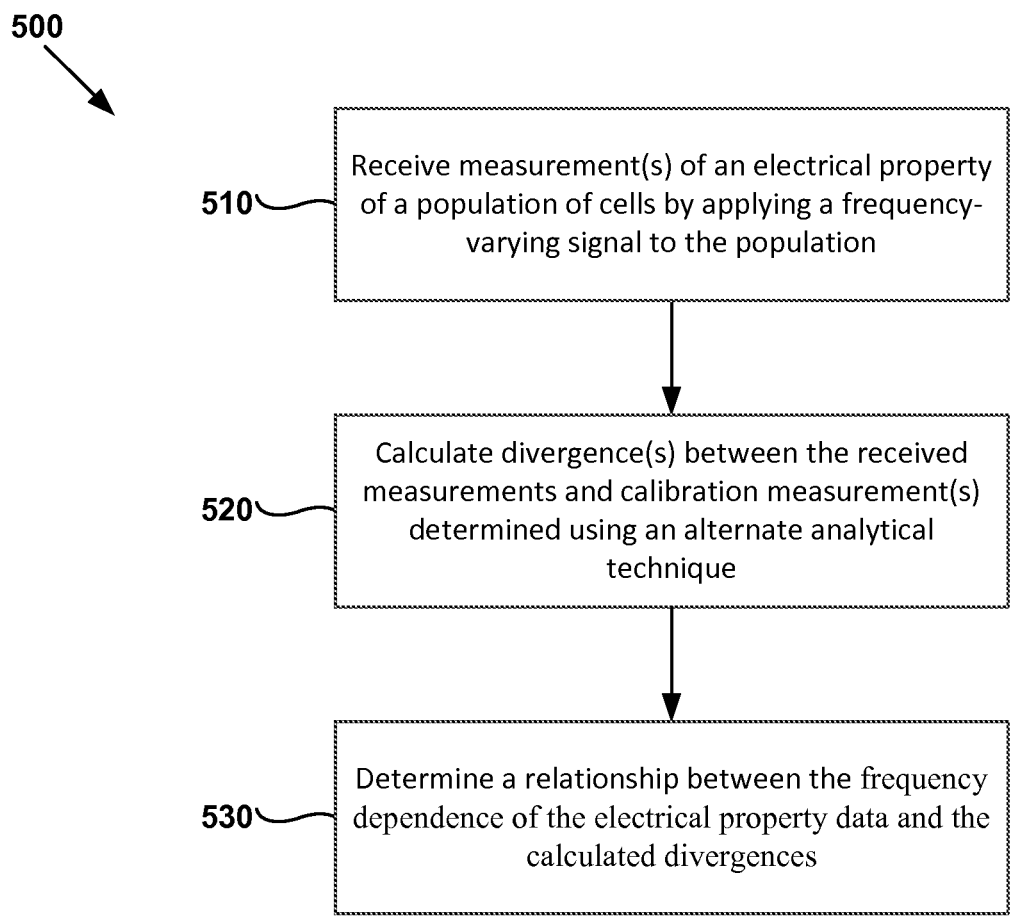

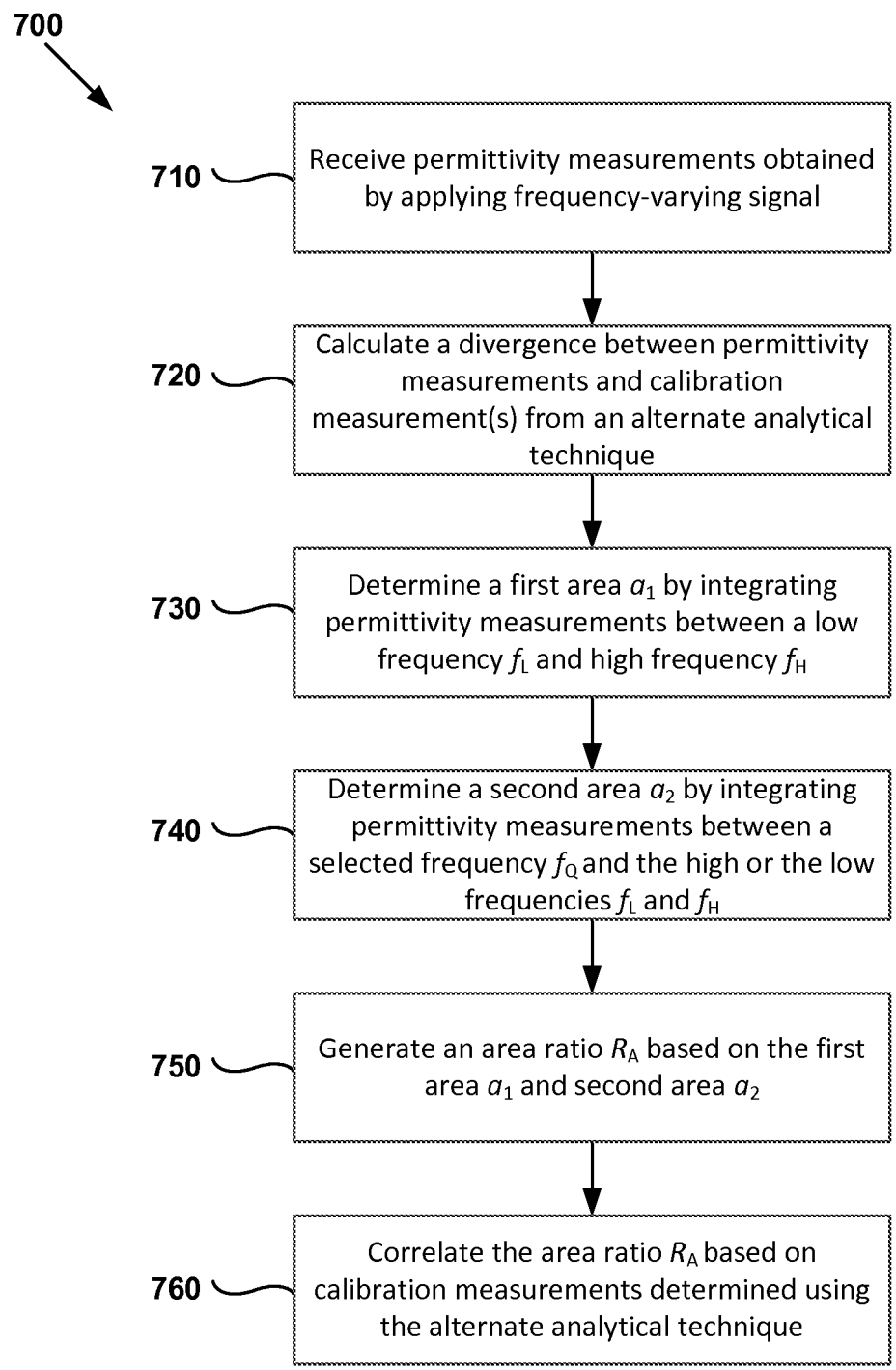

$$\varepsilon_N = \frac{\varepsilon}{\varepsilon_{max}}$$

$$R_A = \frac{\int_{f_Q}^{f_H} \varepsilon(f)df}{\int_{f_L}^{f_H} \varepsilon(f)df}$$

$$R_A = \frac{\int_{f_L}^{f_Q} \varepsilon(f)df}{\int_{f_L}^{f_H} \varepsilon(f)df}$$

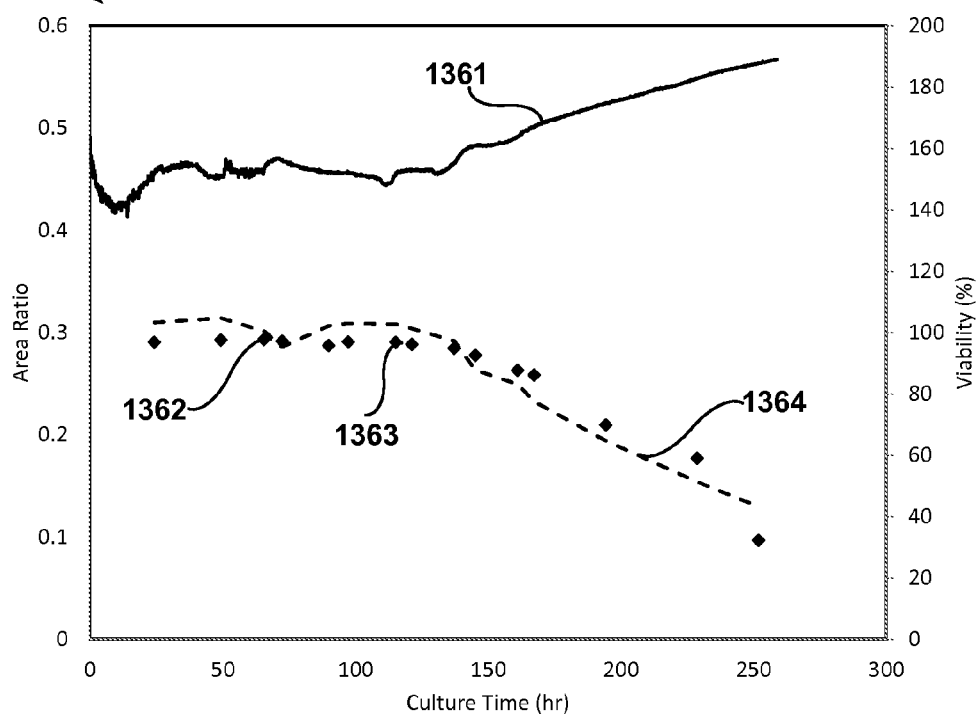
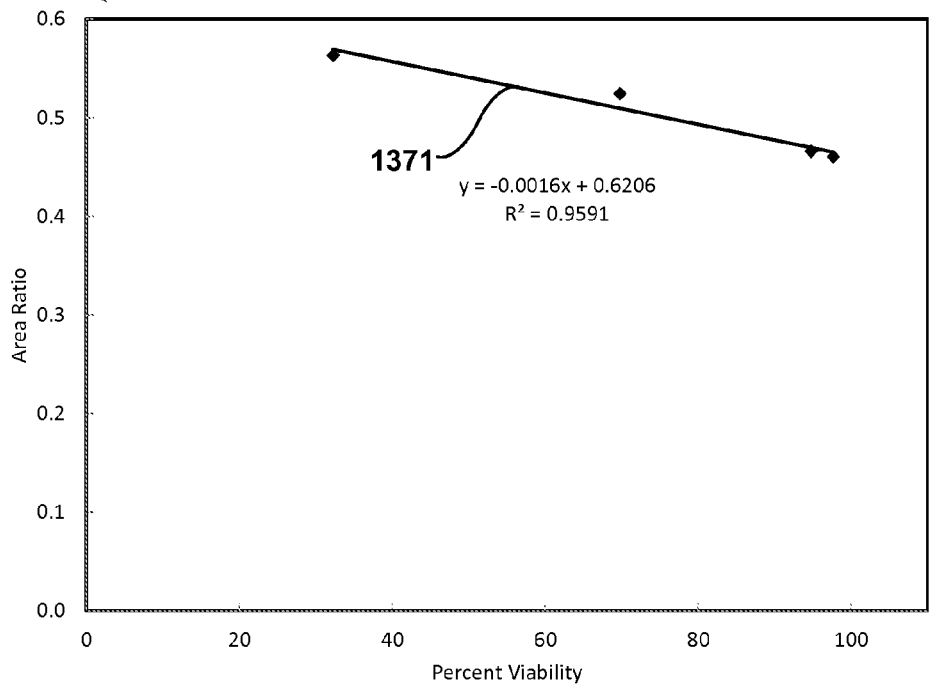

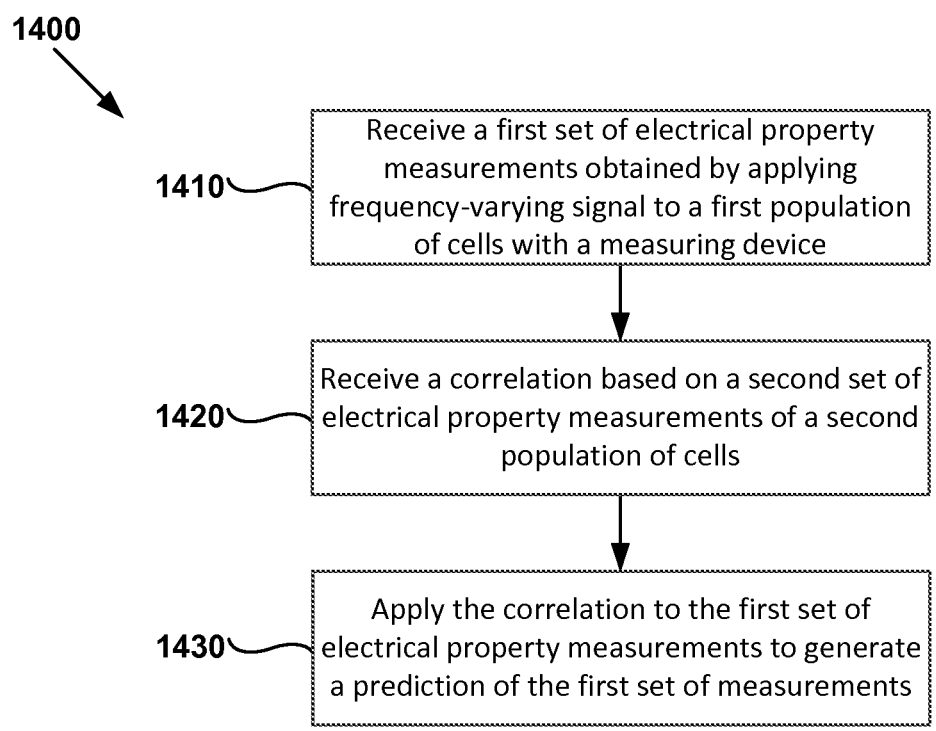

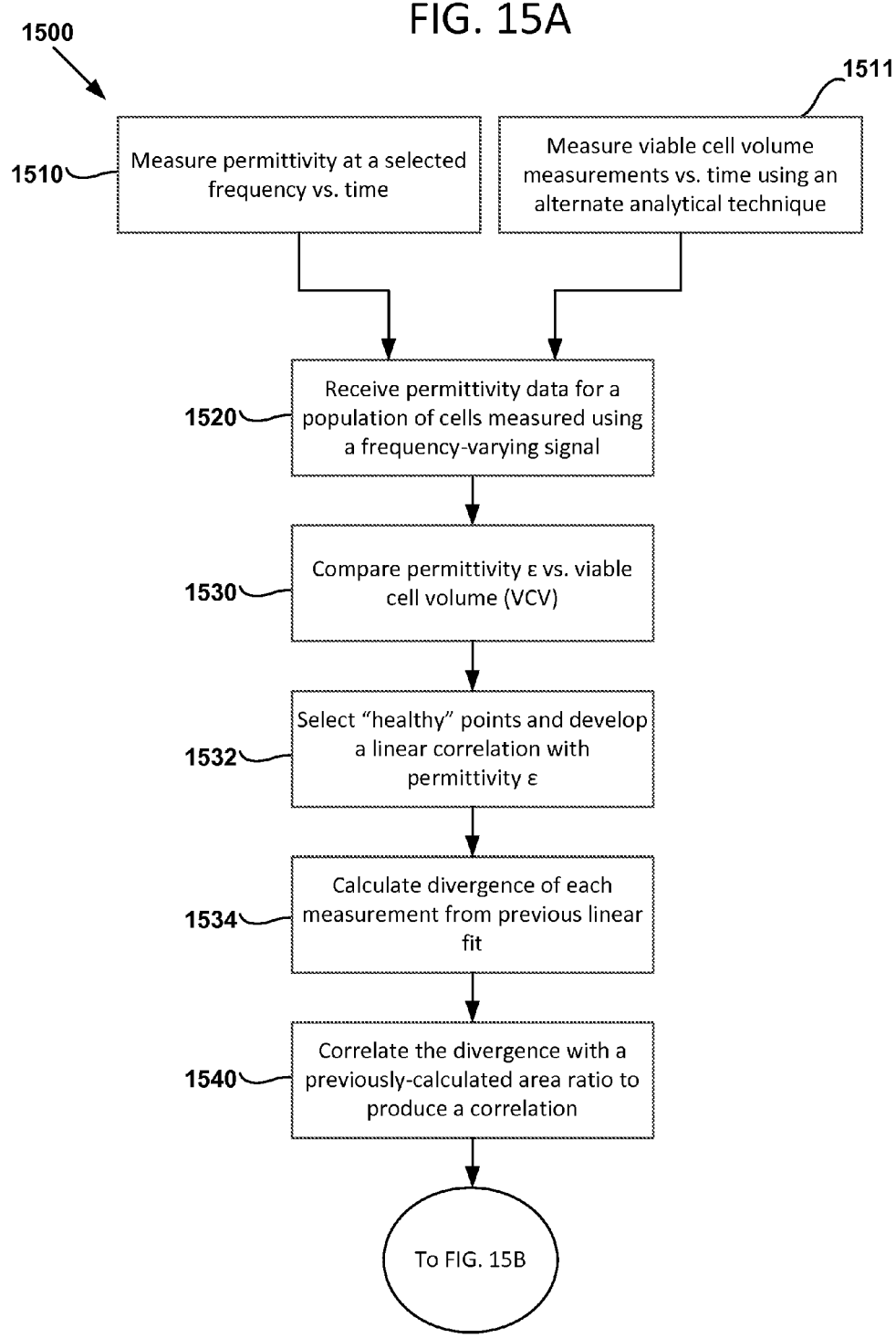

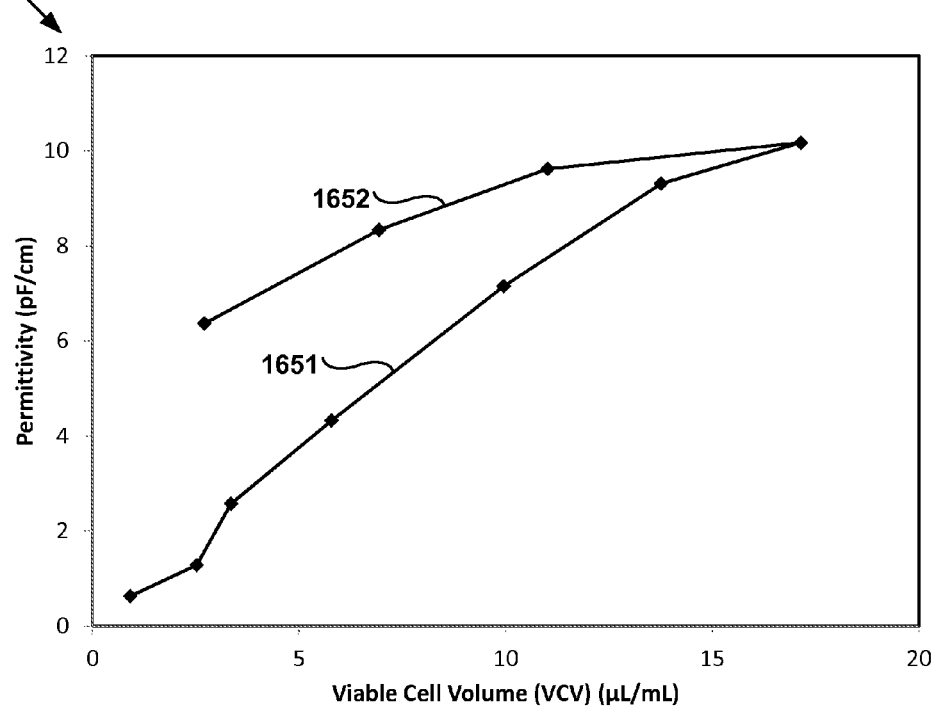
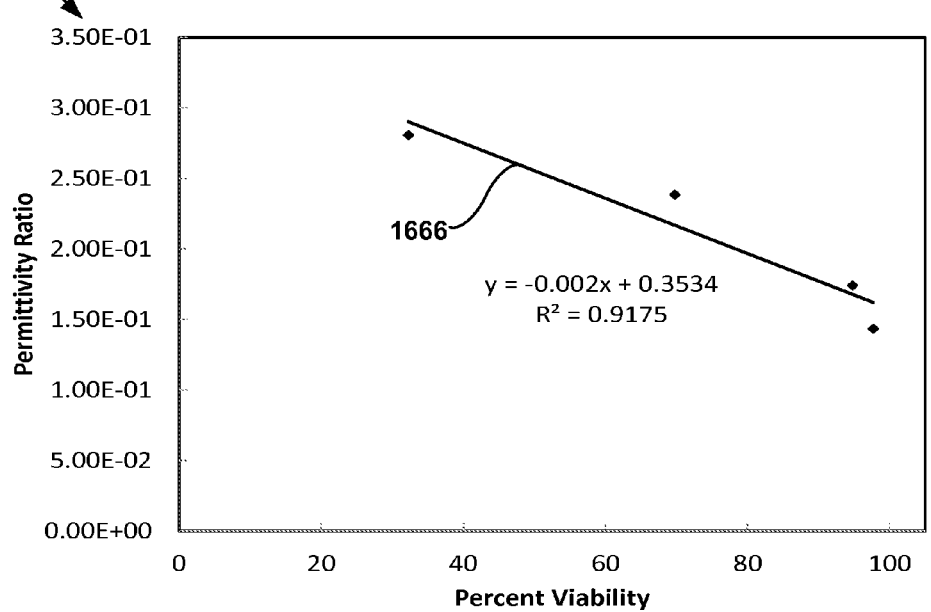

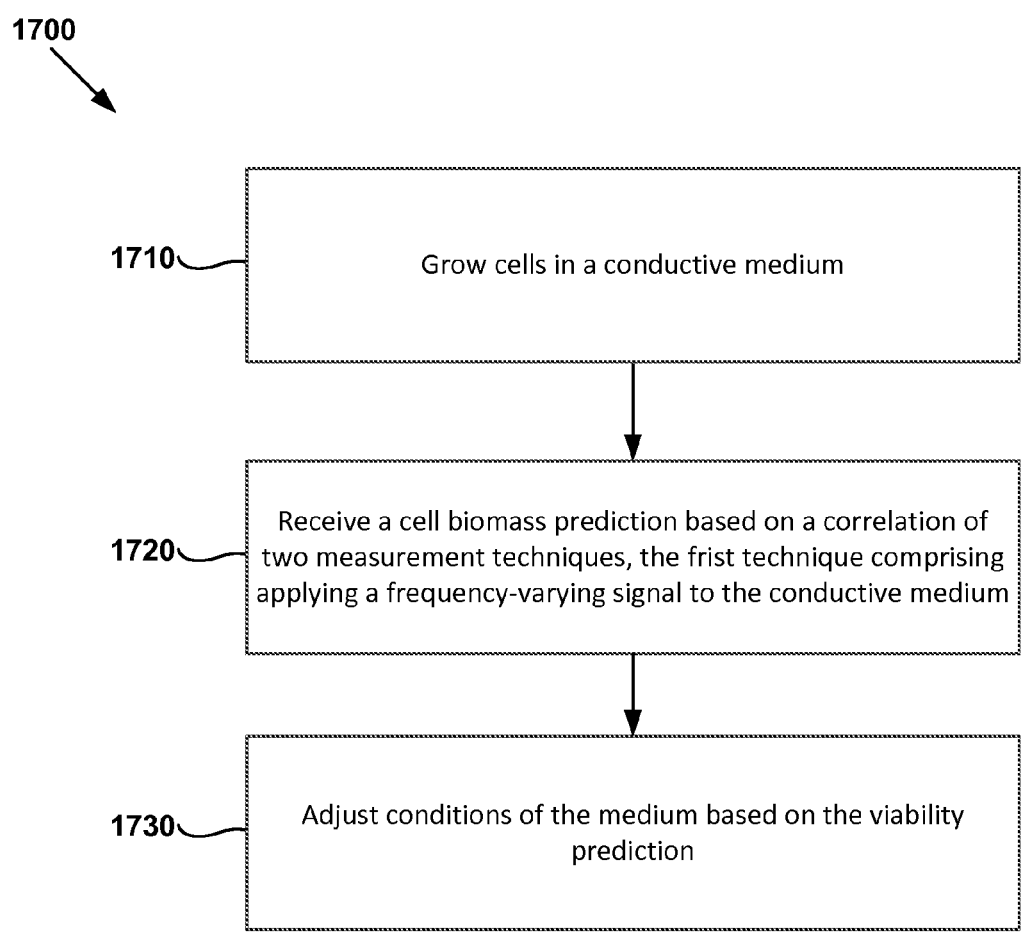

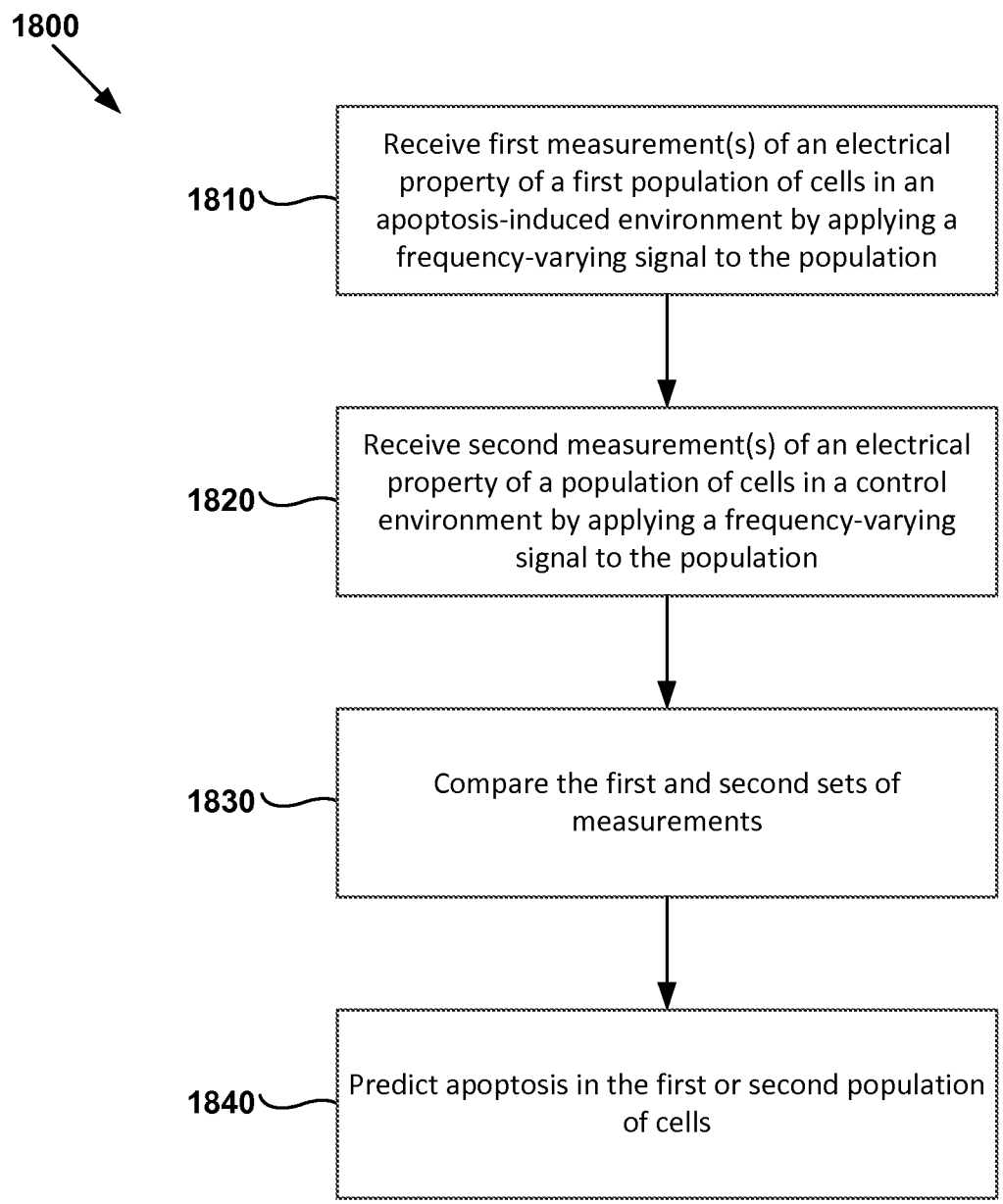

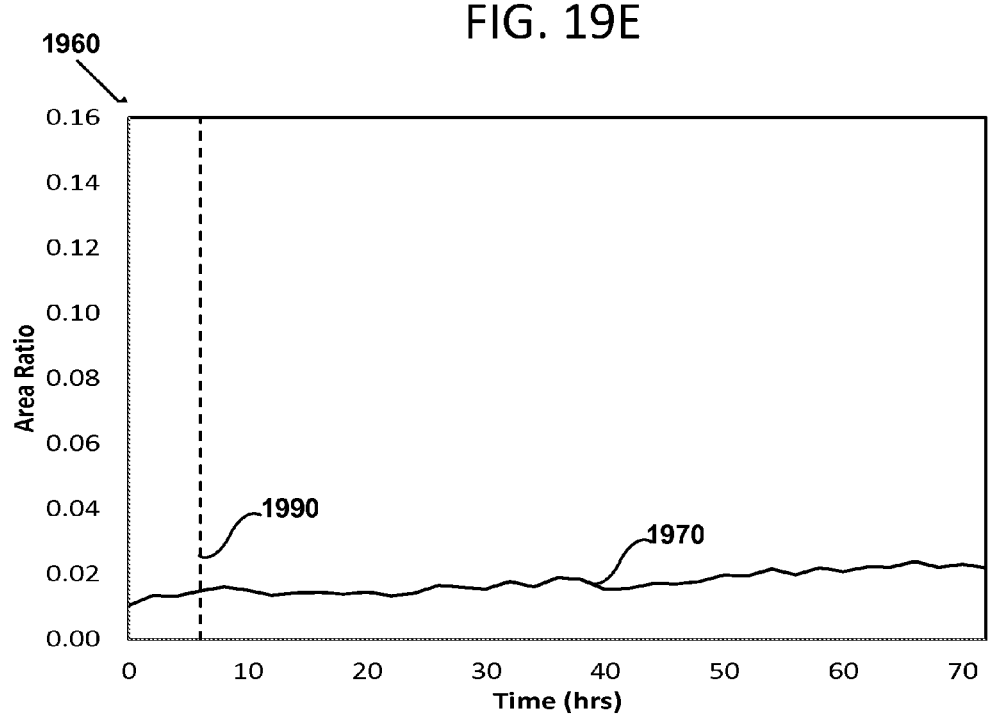
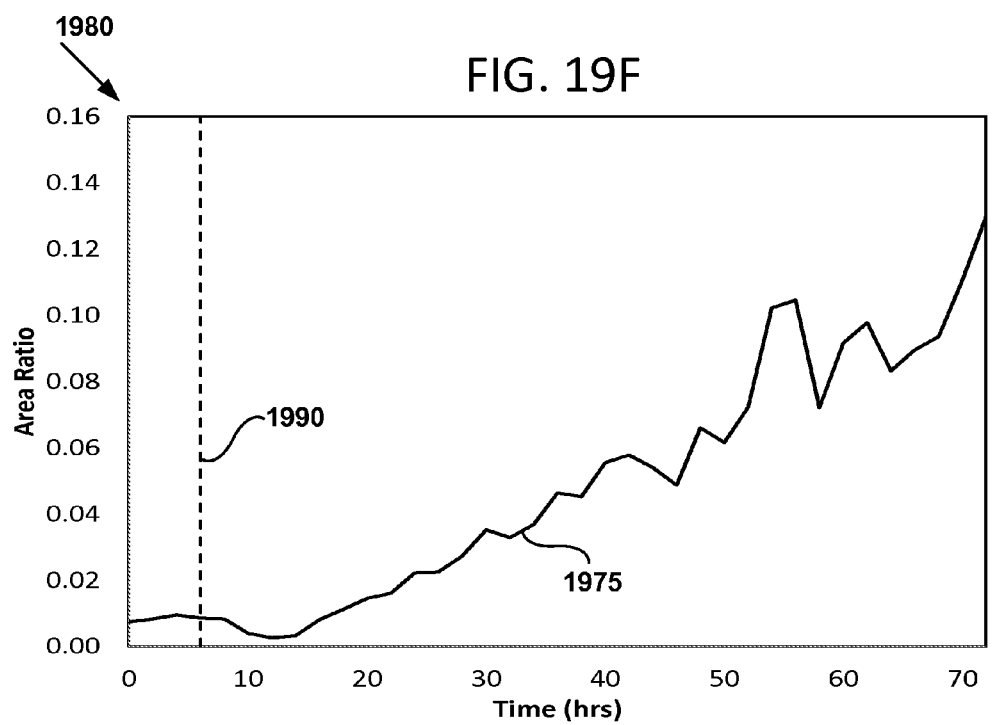

FIG. 22B
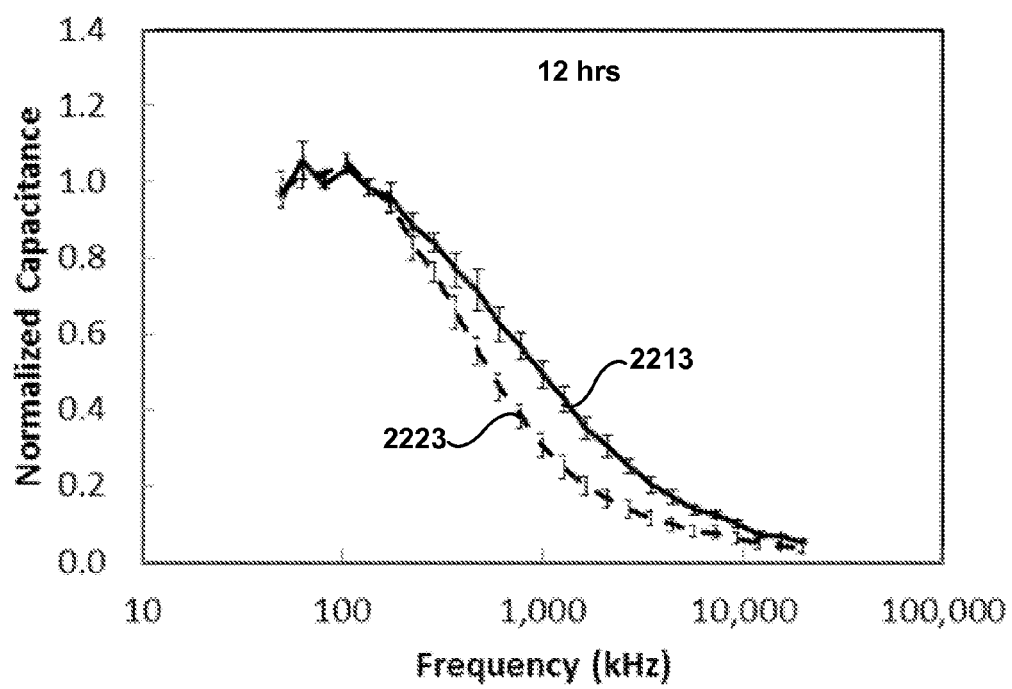
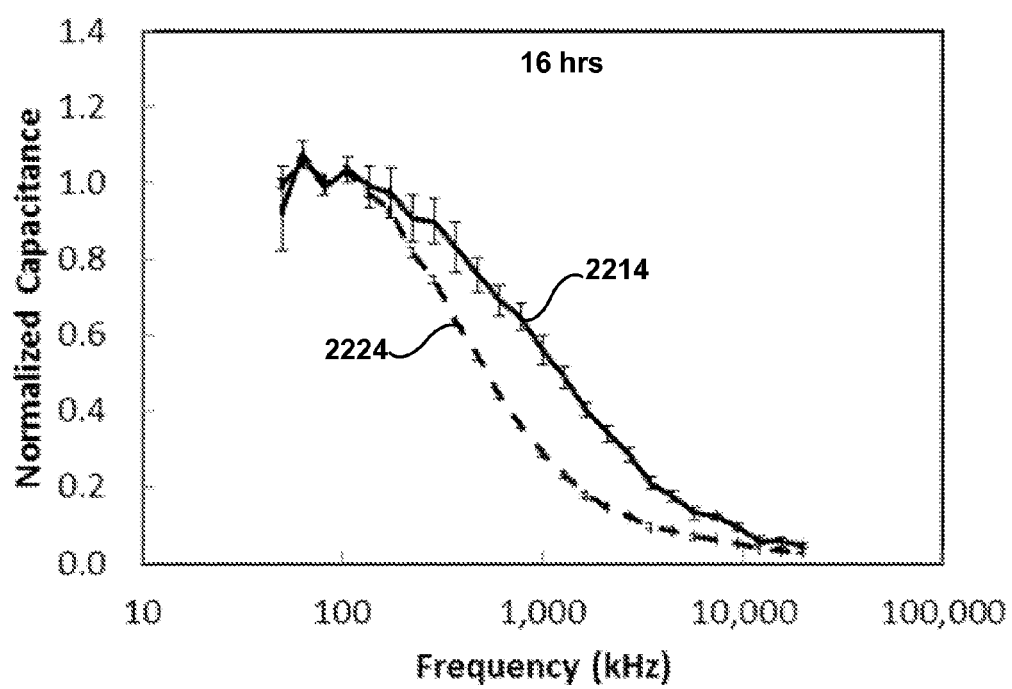

FIG. 22C
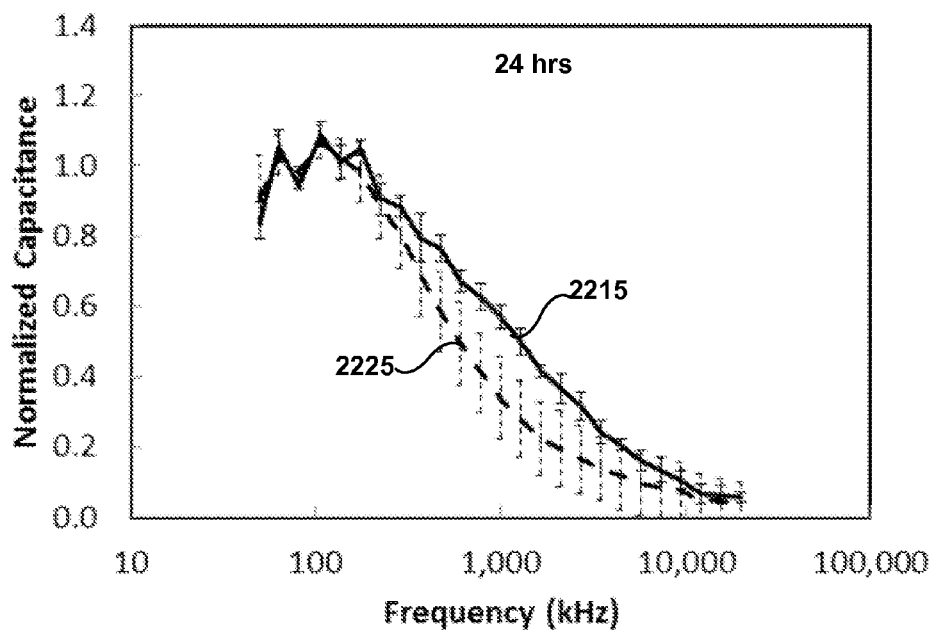
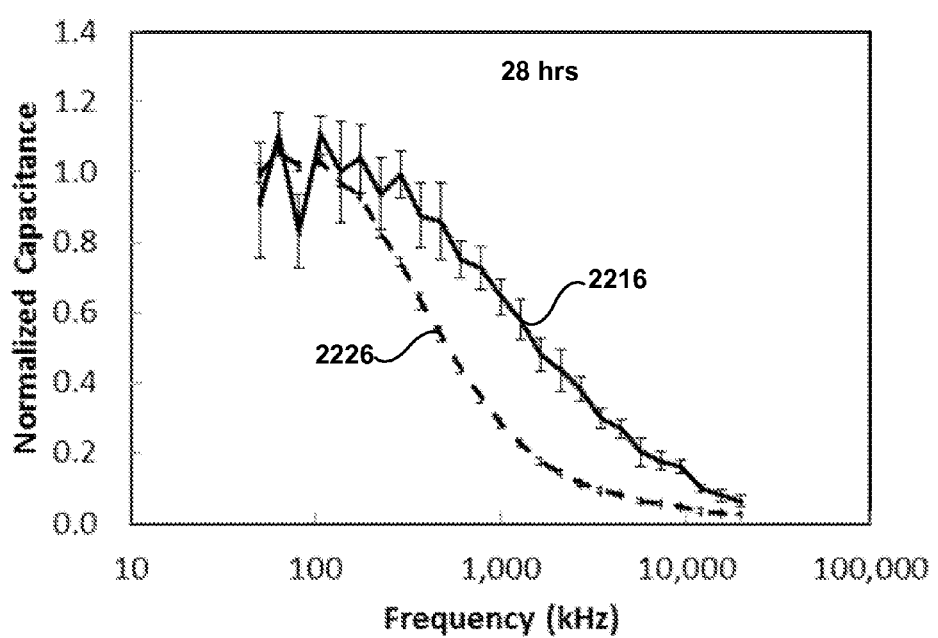

DIELECTRIC SPECTROSCOPY METHODS AND APPARATUS

CROSS-REFERENCE TO RELATED APPLICATIONS

This is the U.S. National Stage of International Application No. PCT/US2013/020397, filed Jan. 4, 2013, which was published in English under PCT Article 21(2), which in turn claims the benefit of U.S. Provisional Application No. 61/584,141, filed Jan. 6, 2012, entitled "DIELECTRIC SPECTROSCOPY METHODS AND APPARATUS"; U.S. Provisional Application No. 61/699,805 filed Sep. 11, 2012, entitled "DETECTION OF APOPTOSIS USING DIELECTRIC SPECTROSCOPY"; and U.S. Provisional Application No. 61/703,103, filed Sep. 19, 2012, entitled "DIELECTRIC SPECTROSCOPY METHODS AND APPARATUS"; all of which are hereby incorporated herein as if set forth fully in their entirety.

FIELD

The disclosed technology relates to methods and apparatus for predicting biological properties, such as viable biomass in a population of cells using an electrical signal.

BACKGROUND

Traditionally, cell counting is performed by mixing an aliquot of a population of cells with trypan blue dye and counting cells disposed on a hemocytometer stage using a microscope. The viable cell density is then determined by visual counting methods. Such hemocytometer techniques are error-prone and require a manual sample of the bioreactor contents. Consequently, a number of alternate analytical techniques have been developed, including techniques that count cells based on electrical impedance as well as techniques that use trypan blue exclusion.

Dielectric spectroscopy (DS) techniques measure the electrical impedance of a sample by applying a time-varying signal to the sample via electrodes. DS techniques can provide information about cell structure and properties, including intracellular contents, membrane shape and polarizability, and other cellular properties.

The dielectric properties of biological cells can provide information regarding the cellular and molecular state of a given population of cells. The dielectric properties of biological cells are mainly characterized by the beta-dispersion, a dielectric relaxation phenomenon, which is observed in the medium and high frequency (HF) range of the radio spectrum. The beta-dispersion mechanism is due to Maxwell-Wagner polarization (interfacial polarization) at the external and internal interfaces of the phospholipid membrane, and is caused by the ability of biological cell membranes to impede electrical current. Additional contributions to the beta-dispersion may be observed due to the presence of organelles, heterogeneity of the cell population, and other phenomena.

DS techniques to estimate dielectric properties of biological cells are discussed at, for example, U.S. Pat. Nos. 4,810,650, 4,965,206, 6,496,020, 6,596,507, and 7,930,110. In the known techniques to estimate biological property data, electrical property data are received by applying a signal to a solution of cells across multiple frequencies.

A need exists for non-destructive screening techniques to associate physical cell-specific phenomena with cell and molecular biology phenomena. Cell-based screening is a powerful method that uses living cells to test the effect of different nutrients, toxicants, and environmental factors on the cellular and molecular phenotype of cells. Thus, there is ample opportunity for the development of tools that permit systematic prediction of cell viability characteristics.

SUMMARY

The disclosed technology relates to methods and apparatus for determining a biological property, such as viable biomass, using a frequency-swept electrical measuring device (e.g., a permittivity probe), and using biological properties, such as viable biomass as measured by an alternative analytical technique (such as trypan blue dye exclusion (e.g., viable biomass measured using an automated cell counter)) as a calibration.

Methods and apparatus are disclosed for correlating a viable cell volume as measured by trypan blue dye exclusion and a viable cell volume as determined by capacitance-based methods. Certain embodiments of these techniques use information measured across a dielectric spectrum to estimate the viable cell volume a priori.

Devices to measure the impedance of a sample can be used to predict biomass by measuring the change in capacitance of a system. These measuring devices also have the capability to measure a dielectric spectrum by measuring relative permittivity of a system using signals applied across a number of different frequencies. With some forms of biomass, when the viability of the culture begins to decrease, the accuracy of using measured capacitances of the system to predict viable biomass begins to diverge in comparison to other methods (e.g., trypan blue exclusion). A divergence in the value measured between the two methods is observed that is roughly proportional to the viability of the culture. This divergence can be interpreted as being caused by cells that cannot exclude the dye in the trypan blue exclusion method retaining intact, or partially intact, cell membranes. This cell membrane retention produces a residual capacitance signal, even though these cells are considered nonviable according to trypan blue dye exclusion.

Dielectric spectroscopy is a non-invasive technique that can be used to illuminate cell-level behavior, for example, in bioreactor cell growth processes. Dielectric spectroscopy can provide a data-rich cell-level snapshot of the cells in a bioreactor. For example, measuring devices used in performing dielectric spectroscopy operate by detecting a capacitance, or ability to store electrical charge, of cells in a population (e.g., a suspension of cells) as a function of frequency applied to the measuring device. This measuring can be accomplished by performing a frequency scan, or in many cases only measuring a single capacitance value. Viable biomass can be predicted via measurement of one or more capacitance values which are indicative of the total magnitude (or intensity, and also called the dielectric increment) of the beta-dispersion curve. The dielectric increment is known to relate directly to biological property data (e.g., total biovolume) of the system via the relationship $$\Delta\varepsilon = \frac{9r\Phi C_m}{4}$$

Where $r$ is the average cell radius, $\Phi$ is the total biovolume, $C_m$ is the membrane specific capacitance, and $\Delta\varepsilon$ is the dielectric increment.

The current state-of-the-art assumes the measured properties are only due to viable cells, and therefore uses a capacitance measurement which is indicative of the dielectric increment to predict biomass as measured by an alternate analytical technique, including offline cell counting methods, such as trypan blue dye exclusion (e.g., using a Cedex analyzer). In the prior art methods, a relationship is determined between the magnitude of the beta-dispersion and a measured biological property.

The relationship is applied to subsequent capacitance measurements to predict biological property data. This prediction generally proves valid when measuring viable biomass when the cells are maintaining a constant viability. The method breaks down, however, when the viability of the cells begin to change, resulting in divergences between the capacitance-based predicted viability and the viability as measured using an alternate analytical technique.

Suitable measuring devices that can be used in performing dielectric spectroscopy are readily discernible to one of ordinary skill in the art. For example, two-terminal electrode, four-terminal electrode, coaxial chamber, single-head dielectric, and multi-wire measuring devices can be used in certain embodiments of the disclosed technology. In some examples, measuring devices include a signal generator, receiver, and signal analyzer coupled to an electrode or probe for measuring electromagnetic properties of a sample. The resulting capacitance(s), or dielectric spectrum, will be affected by cell attributes such as morphology, membrane charge, organelles, health, and/or buildup of metabolites within the cell, and the resulting capacitance(s) can therefore yield information about these attributes in real-time.

In some embodiments, the disclosed technology allows for the accurate measurement of cell viability over the life cycle of a cell culture, not just during the growth phase. This can allow for a feeding scheme where feeds are based on biomass and hence cell demand. For example, extra-cellular reactions of a bioproduct with feed components can produce unacceptable amounts of product impurities, but some amount of feed component must be added to continue to produce the product. Thus, a variable feed based on cell biomass (e.g., viable cell volume) can allow for finer control of feed components in such situations.

In some embodiments of the disclosed technology, exemplary methods for determining a biological property of cells suspended in a liquid media include receiving electrical property data obtained by applying a signal to the cells at two or more signal frequencies, receiving biological property data obtained using an alternate analytical technique, generating at least one value representative of the frequency dependence of said electrical property data, and determining a relationship between said biological property data and said value representative of said electrical property data.

In some examples of these methods, the value representative of the electrical property data represents a shape of the electrical property data relative to frequency. In some examples, the electrical property data and the biological property data are obtained at two or more time points, and representative value is generated at each respective time point. In some examples, the representative value is generated by calculating a ratio from the electrical property data collected at different frequencies.

In some examples of these methods, a representative value is generated by: determining a first area ($a_1$) by calculating an integral of the at least one electrical property between a low frequency ($f_L$) of the signal and a high frequency ($f_H$) of the signal; determining a second area ($a_2$) by calculating an integral of the at least one electrical property between a selected frequency ($f_Q$) and the high frequency ($f_H$) or between the selected frequency ($f_Q$) and the low frequency ($f_L$), the selected frequency ($f_Q$) being greater than the low frequency ($f_L$) and less than the high frequency ($f_H$); and calculating an area ratio based on the first area ($a_1$) and the second area ($a_2$).

In some examples of these methods, the representative value is generated using one or more of the following techniques: performing a multivariate analysis of the electrical property data, by determining the slope of a line corresponding to the electrical property data, by determining a ratio of the electrical property data measured at different frequencies, and/or by determining an area ratio under the curve derived from the electrical property data.

In some examples of these methods, the relationship comprises a correlation between the biological property data and the electrical property data. In some examples, the relationship is determined based on a divergence between the magnitude of the electrical property data and the biological property data. In some examples, the relationship is applied to subsequent electrical property data taken from a new population of cells to predict biological property data for the new population of cells.

In some examples of these methods, the representative value is representative of both a magnitude and the frequency-dependence of the electrical property data. In some examples, a magnitude of the electrical property data is determined, and the value is used together with the magnitude to determine the biological property of said cells.

In some examples of these methods, the electrical property data includes at least one or more of the following: capacitance, permittivity, dielectric constant, resistance, impedance, voltage, or current. In some examples, the biological property data includes at least one or more of the following: viable cell volume (VCV), packed viable cell volume (PVCV), viable cell density (VCD), viable cell concentration (VCC), viability, cell health, and the level of apoptosis.

In some examples of these methods, the relationship is used to adjust one or more environmental conditions of the cells.

Some examples of these methods include growing cells in a conductive medium; receiving a prediction of the viability of the cells, the prediction having been determined based on a correlation between a predicted apoptosis level determined using a first measurement technique and measurements determined using a second measurement technique, the second technique comprising applying a frequency-varying signal to the conductive medium; and based on the viability prediction, adjusting the conditions of the conductive medium.

In some examples of these methods, an apparatus includes a measuring device configured to apply the signal to the cells, processing resources coupled to said measuring device, and computer-readable storage media storing computer-readable instructions that when executed by the processing resources cause the apparatus to perform the method of one or more of the foregoing embodiments.

This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will

BRIEF DESCRIPTION OF THE DRAWINGS

FIG. 4 is a flow chart that illustrates a method for combining measurements of the magnitude and shape of the electrical property data for obtaining a new correlation to predict biological property data in subsequent tests.

FIG. 5 is a flow chart that illustrates a generalized example of a method of calculating divergences between received measurements and calibration measurements.

FIG. 7 is a flow chart that illustrates a generalized example of a method of correlating divergences for a number of permittivity measurements.

FIG. 8A is a graph illustrating a series of permittivity versus frequency curves (spectra) taken at different time points, while

FIGS. 13A and 13B are graphs illustrating experimental results obtained using exemplary methods of predicting viable cell volume obtained in accordance with the disclosed technology.

FIG. 14 is a flow chart that illustrates a generalized example for determining relationships between biological property data and electrical property data of cells.

FIGS. 15A-B illustrate a flow chart for a further detailed example of correlating and applying divergences of viable cell volumes calculated using an alternate analytical technique.

FIGS. 16A-E are charts illustrating experimental results obtained using exemplary methods of predicting viable cell volume obtained in accordance with the disclosed technology.

FIG. 17 is a flow chart that illustrates a generalized example of a method of growing cells in a conductive medium.

FIG. 18 is a flow chart that illustrates a generalized example of a method of comparing measurements between two populations of cells, as can be used in certain embodiments of the disclosed technology.

FIGS. 19A-F are graphs illustrating various measurements obtained over time for cell populations as can be observed using the method outlined in FIG. 18.

FIGS. 22A-C are a series of graphs illustrating changes in dielectric spectra that can be observed in certain examples of the disclosed technology.

DETAILED DESCRIPTION

Figure 1:
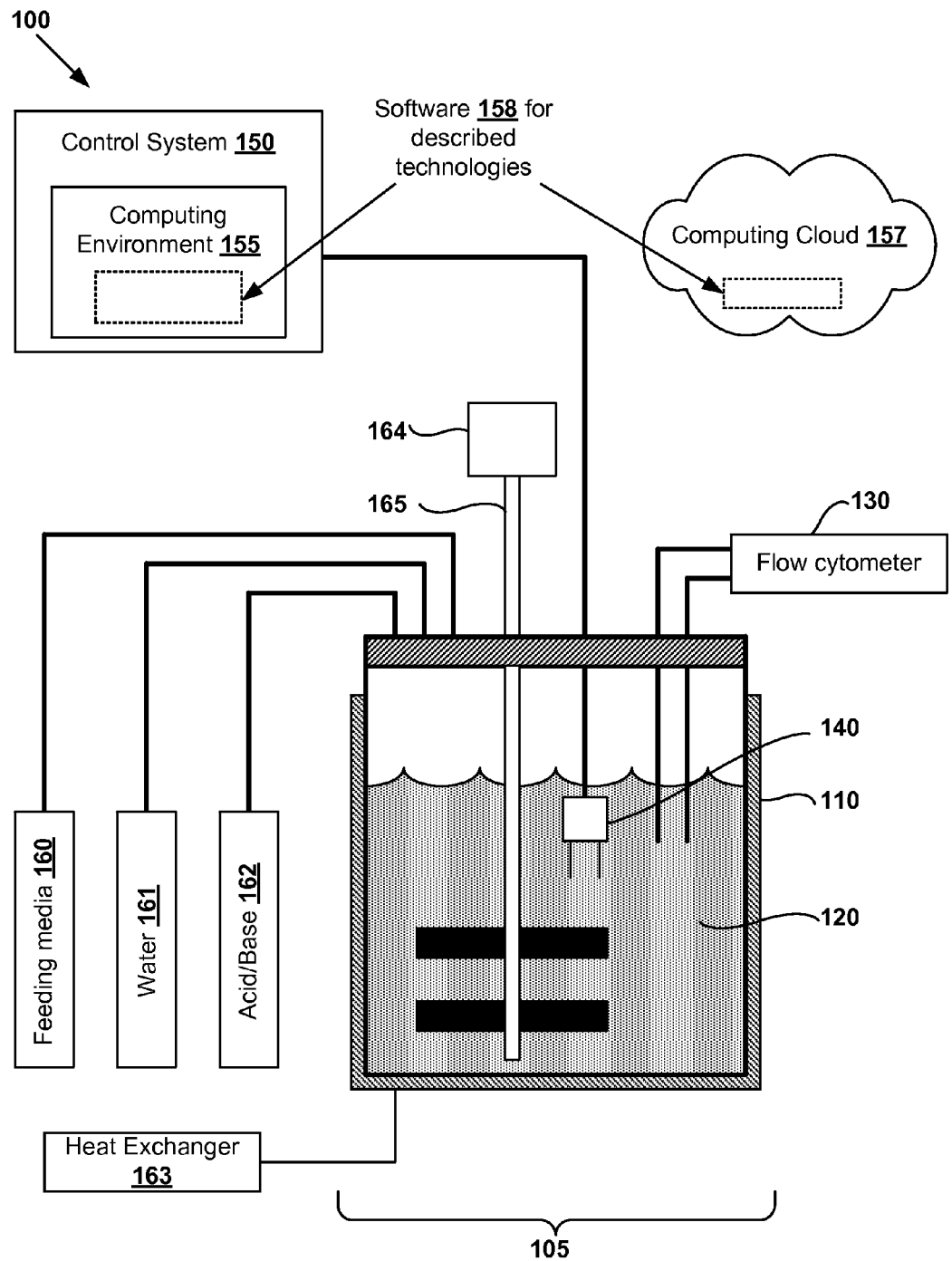
FIG. 1 is a schematic of a suitable system in which described embodiments, techniques, and technologies can be implemented.

This disclosure is set forth in the context of representative embodiments that are not intended to be limiting in any way.

As used in this application and in the claims, the singular forms "a," "an," and "the" include the plural forms unless the context clearly dictates otherwise. Additionally, the term "includes" means "comprises."

The systems, methods, and apparatus disclosed herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Furthermore, any features or aspects of the disclosed embodiments can be used in various combinations and sub-combinations with one another. Furthermore, as used herein, the term "and/or" means any one item or combination of items in the phrase.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged, omitted, or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "receive," "produce," "calculate," "predict," "apply," "determine," "generate," "associate," "select," "search," and "provide" to describe the disclosed methods. These terms are high-level abstractions of the actual operations that are performed. The actual operations that correspond to these terms can vary depending on the particular implementation and are readily discernible by one of ordinary skill in the art.

Some of the disclosed methods can be implemented with computer-executable instructions stored on one or more computer-readable storage media (e.g., non-transitory computer-readable media, such as one or more volatile memory components (such as DRAM or SRAM), or nonvolatile memory components (such as hard drives) and executed on a computer. Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially-available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. Likewise, the disclosed technology is not limited to any particular computer or type of hardware. Certain details of suitable computers and hardware are well-known and need not be set forth in detail in this disclosure.

Theories of operation, scientific principles, or other theoretical descriptions presented herein in reference to the systems, methods, and apparatus of this disclosure have been provided for the purposes of better understanding and are not intended to be limiting in scope. The systems, methods, and apparatus in the appended claims are not limited to those systems, methods, and apparatus that function in the manner described by such theories of operation.

Unless otherwise specified, the terms "capacitance" and "permittivity" are treated as equivalent for the purposes of the present disclosure, for reasons that will be readily apparent to one of ordinary skill in the relevant art. Further, unless otherwise specified, the terms "viable biomass," "viable cell volume," "biovolume," and "viable volume fraction" are treated as equivalent for the purposes of the present disclosure, for reasons that will be readily apparent to one of ordinary skill in the relevant art.

As used in this application and in the claims, the term "magnitude" refers to the intensity, or distance between the low and high frequency plateaus, of the beta-dispersion curve obtained when measuring an electrical property of a sample of cells. As used in this application and in the claims, the term "frequency dependence" refers to a relation between the frequency of a signal applied to a sample of cells to measure an electrical property and the measurements of the electrical property thereby obtained.

Any trademarks used herein are used for illustrative purposes only and are the property of their respective owners.

INTRODUCTION

Devices to measure the electrical properties of a population of cells can be used to predict biological property data (e.g., cell viability characteristics and biomass characteristics such as viable cell volume (VCV)) by measuring changes in capacitance and/or permittivity of a system. These measuring devices (e.g., permittivity probes) can scan across various frequencies and create a dielectric spectrum. However, with some types of cells, divergences between the capacitance-based predicted viability and the viability as measured by trypan blue exclusion (e.g., using a Cedex analyzer) are observed.

In one example of the disclosed technology, in order to compensate for this disparity, frequency scanning data are collected over time in a fed-batch culture of cells (e.g., mammalian cells). The frequency scans are normalized (e.g., to a range of 0.0 to 1.0) by dividing the measured permittivity values by the maximum measured permittivity value. A difference in the relative shapes of the beta-dispersion curves (e.g., the dielectric spectrum consisting of measured permittivity as a function of frequency) is observed in the high frequency region during the decreasing viability phase of the culture lifetime (the phase where the divergence is observed). This shape difference in the beta-dispersion can be quantified by taking an integral ratio of the upper portion of the curve compared to the whole curve for a plurality of time points.

In one embodiment, the integral ratio value is then correlated to the observed divergence between the trypan blue exclusion and capacitance values. The observed correlation tends to be linear. This correlation can be used to correct for divergences observed during subsequent runs, as the slope and intercept remains relatively constant between runs. Thus, embodiments of the disclosed technology allow for accurate measurements of cell viability characteristics (e.g., viable cell volume) over the entire lifetime of the culture, not just during the growth phase.

Example Bioreactor for Use in Predicting Cell Health and Viability

FIG. 1 is a schematic of a suitable system 100 for growing a culture of cells in accordance with some embodiments of the disclosed technology. Viability of the culture cells can be predicted using, for example, any of the methods described in FIGS. 2-9 and accompanying descriptions.

As shown in FIG. 1, an exemplary bioreactor system 100 for making a bioproduct includes a bioreactor 105 having a vessel 110 capable of providing an aseptic environment suitable for containing a population of cells 120 that can produce the bioproduct. The population of cells 120 contains media and at least one undissolved species, either as a suspension or adhered to a substrate. In some examples, the population of cells 120 includes a mixture of cells dispersed in a liquid media (forming a suspension). The system 100 also contains a sampling system 130 (e.g., a flow cytometer) operably connected to the vessel 110 and capable of extracting a sample from the vessel. The system 100 also includes a measuring device 140 (e.g., a permittivity probe, or other measuring device suitable for measuring an electrical property of the population of cells 120) operably connected to the vessel 110, the measuring device being configured to measure an electrical property of the population of cells 120 in the vessel and generate a corresponding signal in response.

A control system 150 is provided that includes a computing environment 155, and, in some examples, the control system can transmit and receive data and/or computer-readable instructions from computing resources in a computing cloud 157. Software 158 for implementing the described technologies, including computer-readable instructions, can be stored on a computer-readable storage medium in the computing environment 155 and/or computing cloud 157. The control system 150 can use the computing environment 155 to analyze signals received from the measuring device 140 and generate output signal(s) capable of controlling one or more input and/or output devices 160-165 that are configured to measure or alter environmental conditions within the vessel 110. For example, devices 160-162 can be used for controlling and/or removing: feeding media, water, and acid or base solutions, respectively. A heat exchanger 163 can be used to heat or cool the vessel 120. A motor 164 is connected to an impeller shaft 165, which can be used to agitate the population of cells 120 (or to agitate the media in the bioreactor). In other examples, a magnetic impeller or other suitable stirring/agitation mechanism can be used. Not all signal and power connections between the devices 160-165 and the control system 150 are depicted in FIG. 1.

In some embodiments, the bioproduct is selected from foods, beverages, biofuels, bioenergy, bio-based ethanol, biodiesel, bio-based adhesives, biochemicals, biotherapeutics, biodegradable plastics, or mixtures thereof. In other embodiments, the bioproduct is a biotherapeutic. In still other embodiments, the bioproduct is a biotherapeutic selected from pharmaceuticals, therapeutic proteins, protein fragments, antibodies, vaccines, or mixtures thereof.

In some examples, the vessel is selected from anaerobic fermenters, aerobic fermenters, stirred-tank reactors, adherent bioreactors, wave-type bioreactors, and disposable bioreactors.

In some examples, the population of cells comprises live cells, dead cells, cell fragments, solid substrates having cells adhered thereto, particles, or mixtures thereof. The live cells can include bacteria, yeast, animal cells, mammalian cells, *e-coli* cells, or mixtures thereof. In some embodiments, the population of cells includes animal cells. In other embodiments, the population of cells includes mammalian cells.

In some examples, biological properties of the population of cells can be selected by adjusting media-level properties and/or cell-level properties. In some embodiments, properties of the population of cells that can be measured and/or adjusted include viable cell volume (VCV), packed viable cell volume (PVCV), viable cell density (VCD), viable cell concentration (VCC), viability, cell health, or mixtures thereof. In other embodiments, properties of the population of cells that can be adjusted include pH, dissolved oxygen, osmolality, nutrient concentrations, ammonia/ammonium, lactate/lactic acid, pCO2, electrolytes (such as K+, Ca++, and/or Na+), amino acids, NAD/NADH, impurities, purity, phenotypes, metabolic states, cell cycle, or mixtures thereof.

In some examples, suitable input devices that can be coupled to the control system 150 include pH probes, dissolved oxygen meters, ion-selective electrodes, osmometry devices, high-performance liquid chromatographs, gas chromatographs, ion chromatographs, conductivity meters, Raman spectroscopes, near infrared spectroscopes, dielectric spectroscopes, fluorometers, ultraviolet/visible spectroscopes, capacitance probes, luminescence meters, redox probes, flow cytometers, hemocytometers, electro-rotators, electrophoresis probes, dielectrophoresis probes, or mixtures thereof.

In some examples, suitable output devices that can be configured to alter at least one property of the population of cells include mixing/agitation systems, temperature-control systems, gas pumps, nutrient pumps, product removal systems, impurity removal systems, pH adjustment systems, or mixtures thereof.

In some embodiments, the control system 150 is configured to alter at least one property of the population of cells within the vessel resulting in an improvement in at least one of bioproduct yield, bioproduct purity, bioproduct production rate, reduced cost, reduced energy consumption, or reduced waste generation, relative to a system that is controlled manually. In some embodiments, an aseptic sampling system is operably connected to the control system.

Bioproducts are made in bioreactors, which are systems that support a biologically active environment. Examples of bioreactors include fermenters (anaerobic or aerobic), stirred-tank reactors, adherent bioreactors, wave-type bioreactors, and disposable bioreactors. A bioreactor can include, for example, a large fermentation chamber for growing organisms that can be used to produce bioproducts.

Bioreactors generally contain whole broth comprising a population of cells. As used herein, the term "whole broth" means the contents of the bioreactor (or a portion thereof), including "media" and "undissolved" or "adhered" species. As used herein, the term "media" means the liquid phase, including all dissolved substances, such as nutrients, dissolved organics, ionic species, etc. As used herein, the term "undissolved" or "adhered" species means the live cells, dead cells, cell fragments, solid substrates having cells adhered thereto, or other particles present in the whole broth.

In some examples, bio-therapeutic proteins can be produced from genetically modified mammalian cells within a bioreactor. Such production can be from cell lines of established cell cultures, such as, for example, CHO or NS0. These cells express the protein of interest and subsequently secrete the protein into the media. In many instances, mammalian cells are grown in a fed-batch process. However, it should be understood that the methods and systems disclosed herein can be applicable in perfusion-type cell culture systems or other such systems.

In some instances, bioreactors can be configured to adjust or control inputs to the bioreactor, including, for example, one or more of the following variables of pH, dissolved oxygen (DO), reactant/nutrient concentrations, temperature, or agitation. Such bioreactors can include stirred-tank type reactors, as well as adherent bioreactors, wave-type bioreactors, or disposable bioreactors.

Bioreactors are typically equipped with a means for mixing or agitating the population of cells in the bioreactor, including using mechanical mixing, circulation pumps, shifting baffle plates, mechanical vibration schemes, ultrasonic agitation, acoustic agitators, gas bubble agitators, vortex generators, cavitation pumping, or combinations thereof. Bioreactors also typically are equipped with heat exchangers for maintaining or controlling the temperature in the bioreactor.

Example Method of Calculating Divergences Between Measurements Obtained with Frequency-Varying Signals and Calibration Measurements The present application discloses improved methods of using the frequency dependence of electrical property data measured at two or more frequencies to determine a biological property of cells more accurately than prior art methods that rely only on measurements of the magnitude of an electrical property.

Figure 2:
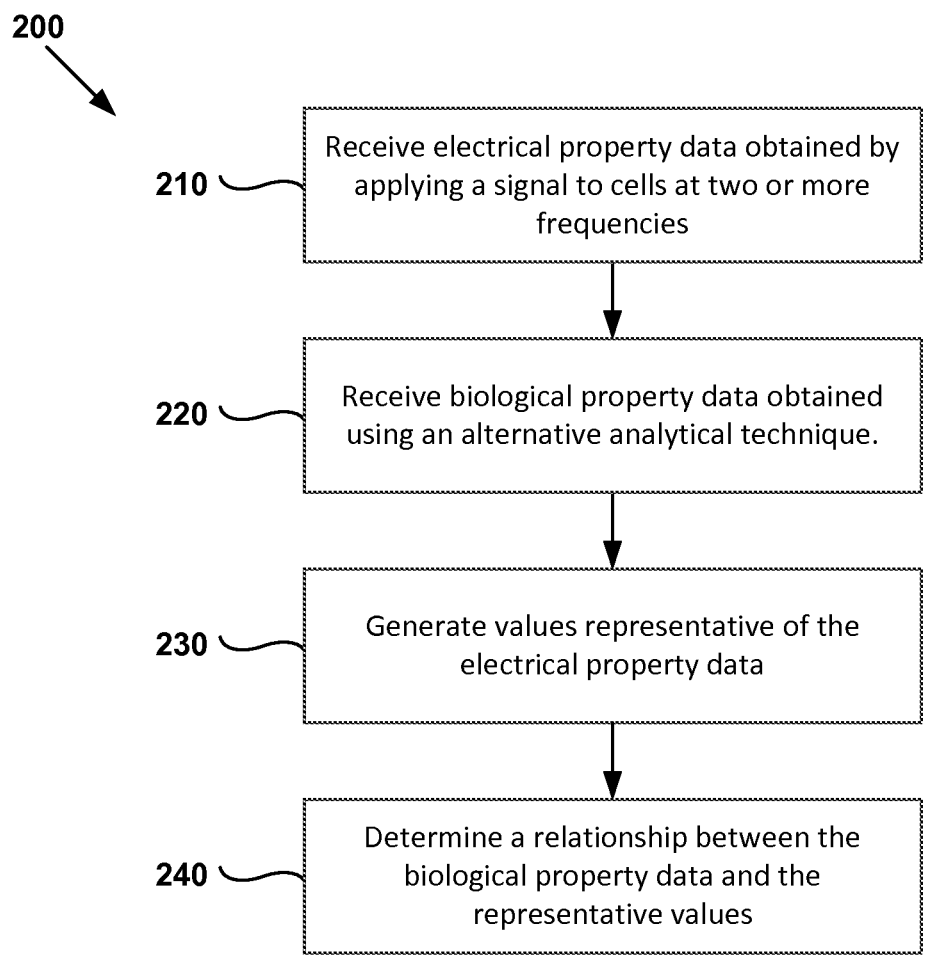
FIG. 2 is a flow chart that illustrates a generalized example for determining relationships between biological property data and electrical property data of cells.

FIG. 2 is a flow chart 200 that outlines an exemplary method of determining a relationship between biological property data for a population of cells and a value representative of electrical property data for a population of cells. In some embodiments, the relationship is determined by applying a correlation of electrical property data obtained at varying frequencies to measurements of biological property data obtained using an alternate analytical technique. In other embodiments, a value representing the frequency dependence of said electrical property data is generated. In other embodiments, a value representative of the relative value of said electrical property data as a function of frequency is generated.

At process block 210, electrical property data are received representing at least one electrical property of a population of cells. The electrical property data can be obtained by applying an electrical signal to the cells at two or more signal frequencies.

The electrical property data can be obtained by applying a frequency-varying signal to a population of cells with a measuring device. Suitable electrical properties that can be measured with a measuring device include capacitance, permittivity, dielectric constant, resistance, impedance, voltage, or current. For example, a permittivity probe capable of applying a number of different frequencies to a suspension of cells in a bioreactor, such as the Futura line of biomass sensors and the Biomass Monitor 200 (manufactured by Aber Instruments of the United Kingdom), and the Fogale Biomass System (manufactured by Fogale Nanotech of France) can be used to measure permittivity or capacitance of the cells when applying a frequency-varying signal. Alternatively, suitable measuring devices include external electrodes placed on the outside or inside of the bioreactor and connected to an appropriate signal generator and receiver.

For example, in some embodiments, the measurements can be obtained by applying a frequency-varying signal (e.g., a sine wave having a frequency that is varied across a selected frequency range, or at two or more selected frequencies) to the population of cells while measuring an electrical property such as permittivity or capacitance. A number of selected frequencies can be used, for example, frequencies between 50 kHz and 10 MHz. The measured permittivity of the population of cells will vary depending on the frequency of the applied signal used to measure permittivity. For example, the permittivity can range from a high measurement of $4 \times 10^{-9}$ Farads per meter (F/m) at a low frequency of 50 kHz to a low measurement of $1 \times 10^{-11}$ F/m at a high frequency of 10 MHz. As used herein, the terms "low frequency" and "high frequency" are relative, and do not necessarily refer to an absolute low or high frequency.

After receiving the electrical property data, the method proceeds to process block 220.

At process block 220, biological property data for measurements observed in the cells are obtained using an alternative analytical method. Exemplary biological property data include viable cell volume (VCV), packed viable cell volume (PVCV), viable cell density (VCD), viable cell concentration (VCC), viability, cell health, level of apoptosis, or mixtures thereof.

In general, the term "alternate analytical techniques" refers to techniques for obtaining calibration measurements based on analyzing cell biomass in ways other than measuring at least one electrical property of a cell population by applying a frequency-varying signal to the cell population with a measuring device. Alternate analytical techniques suitable for performing such calibration measurements include, but are not limited to: enumeration using a hemocytometer, trypan blue exclusion, caspases for measuring cell apoptosis, fluorescence-activated cell sorting using flow cytometry, or other techniques known to one of ordinary skill in the art.

After receiving the biological property data, the method proceeds to process block 230.

At process block 230, values representative of the electrical property data as a function of frequency received at process block 210 are generated. In one embodiment, the value representative of the electrical property data as a function of frequency can represent a shape. In one embodiment, the shape of the electrical property data refers to the curve obtained from plotting the electrical property data as a function of frequency and thus represents the frequency dependence of the electrical property. An example is the beta-dispersion curve obtained by plotting permittivity versus frequency. The beta-dispersion curve is frequency dependent. Values representative of the shape of the electrical property data are generated by appropriate data reduction over the frequencies at which electrical property data are measured. For example, the representative value may be generated by fitting a curve to the electrical property data, by multi-variate analysis, by determining the slope of a line corresponding to the electrical property data, by determining a ratio of the electrical property data measured at different frequencies, or by determining an area ratio under the curve derived from the electrical property data. In some examples, the representative values represent a shape corresponding to the spectrum of electrical property data taken over two or more signal frequencies at which the respective electrical property data were obtained. In some examples, the representative values represent an area ratio. In some examples, the value representative of the shape can be obtained by fitting the beta-dispersion curve to a mathematical function such as a line, polynomial, Taylor series expansion, or other methods apparent to those familiar with curve fitting, fitting the beta-dispersion curve to a model of physical relevance such as a single or multiple term Cole-Cole model, Debye model, Davidson-Cole model, or Havriliak-Negami model, analyzing the electrical property data using multivariate methods (multi-variate or latent variable analysis), or other methods that are capable of quantifying the shape of a curve.

After generating the representative values, the method proceeds to process block 240.

At process block 240, a relationship between the biological property data and the representative values of the shape of the electrical property data are determined. In some embodiments, the relationship includes a correlation between the biological property data and the shape of the electrical property data, and such a correlation can be determined using the techniques described for process block 230. Thus, the correlation describes the relationship between the shape of the electrical property of the cells measured at two or more frequencies and measurements of biological property data, such as VCV, PVCV, VCD, VCC, viability, cell health, or level of apoptosis.

In some examples of the disclosed technology, the relationship includes a correlation generated based on permittivity measurements received at process block 210 and calibration measurements determined using an alternate analytical technique.

The relationship generated at process block 240 can be applied to generate one or more corrected measurements based on the electrical property data received at process block 210. For example, if the relationship includes a correlation in the form of a slope-intercept equation, the equation can be used to calculate corrected measurements based on the electrical property data. The generated correlation (between the electrical property data and biological property data) can be applied to future electrical property measurements to predict biological property values.

Determine a Relationship Using Two-Frequency Electrical Property Data

Figure 3:
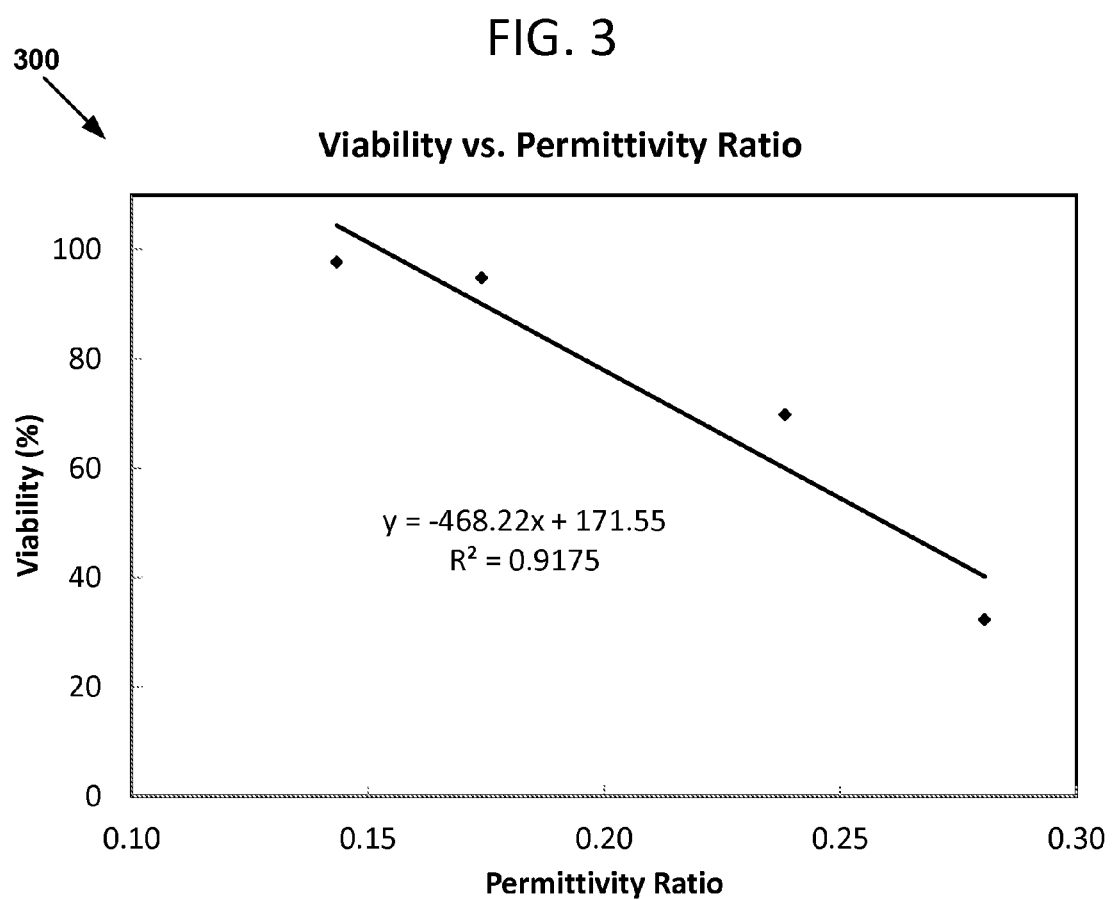
FIG. 3 is a graph illustrating viability versus permittivity ratio for determining a relationship between biological property data and electrical property data obtained at two-frequencies.

In one embodiment, the method of the invention can utilize electrical property data obtained by applying a signal to the cells at two frequencies. FIG. 3 is a graph 300 that indicates a frequency dependence of the electrical property data to frequency by illustrating a plot of cell viability versus a permittivity ratio when using a high frequency of 6.451 MHz, and a low frequency of 1.391 MHz. The data are given in Table 1.

TABLE 1

| | Electrical Property Data | | | Biological Property Data |
|---|---|---|---|---|
| Cell Culture Time (hr) | Permittivity at 6.451 MHz | Permittivity at 1.391 MHz | Value Representative of Electrical Property Data | Cell Viability (%) |
| 66 | 0.054 | 0.377 | 0.14 | 97.7 |
| 137 | 0.066 | 0.377 | 0.18 | 94.8 |
| 194 | 0.114 | 0.479 | 0.24 | 69.8 |
| 252 | 0.156 | 0.556 | 0.28 | 32.3 |

The cell viability can be determined using trypan blue dye exclusion as measured by a flow cytometer.

The value representative of the electrical property data can be determined by taking a ratio of the permittivity measured at the high frequency relative to the permittivity measured at the low frequency.

The relationship between the value representative of the electrical property data (or shape of the beta dispersion curve) and the biological property data (in this case cell viability) can be determined by forming a linear relationship between the permittivity ratio and the cell viability, as shown by the equation shown in FIG. 3. This new correlation can be used to predict biological property data (e.g., cell viability) in subsequent tests.

Example Utilizing Measurements of Both Shape and Magnitude of the Beta-Dispersion to Obtain Enhanced Prediction of Viable Cell Volume FIG. 4 describes a method for combining measurements of both the magnitude and shape of the measured beta-dispersion curve from a calibration experiment to achieve a more accurate prediction of viable biomass compared to using just magnitude alone. In general terms, the magnitude parameter is correlated to the biomass first, a model is fit to that correlation, and the shape parameter is used subsequently to describe the divergence (or distance) of each measurement from the magnitude model.

In process block 410, electrical property data are obtained by applying a signal to cells in a bioreactor at multiple frequencies. These electrical property data are obtained across the beta-dispersion curve such as to allow measurement of both the shape and magnitude (dielectric increment as described above).

In process block 420, the magnitude of the beta dispersion is quantified. Methods for quantifying the magnitude of the beta-dispersion include measurement of permittivity at a single frequency on the beta-dispersion curve, measurement of the difference between the low and high frequency plateaus of the beta-dispersion, or any other methods suitable for quantifying the magnitude of the beta-dispersion curve.

In process block 425, the shape of the beta-dispersion curve is quantified.

In process block 430, the magnitude of the beta-dispersion is related to biological property data obtained using alternative analytical techniques, such as those previously described, and other techniques readily ascertainable to those of ordinary skill in the relevant art.

In process block 440, a relationship between the magnitude of the beta-dispersion and the biological property data is determined. The relationship between the magnitude of the beta dispersion curve and the biological property data can be determined as follows: a linear relationship during all or a portion of the life cycle of the cells, a linear relationship during the growth phase of the cells, or other methods readily apparent to those skilled in the art.

In one embodiment, the relationship between the magnitude of the beta-dispersion curve and the biological property data is a linear model fit to the biological property data during the growth phase. In process block 450, the divergence between the relationship developed in block 440 and the biological property data is determined. In this example, the divergence is calculated by the difference between the biological property data measured by an alternative analytical technique and the predicted biological property data using the linear relationship determined during the growth phase of the cells.

In process block 460, the shape of the beta-dispersion curve from block 425 is combined with the divergence in block 450 to develop a new relationship to predict biological property data.

In process block 470, the new relationship developed from block 460 is used to develop a new correlation to predict biological property data in subsequent tests (e.g., a new population of cells). These correlations (one relating magnitude of the beta-dispersion to biological property data, the other relating shape of the beta-dispersion to divergence from the first correlation) can be used in subsequent measurements of the beta-dispersion obtained from cells to obtain an improved prediction of biological property data from the current state-of-the-art.

The resulting prediction of viable cell volume therefore can be expressed in the form of the following equation:

$$VCV = \alpha \times C + \beta \times SF + k$$

Where VCV is the predicted biological property data (in this case, viable cell volume), $\alpha$ is a constant of proportionality fit to the data, C is a value quantifying the magnitude of the beta-dispersion curve, $\beta$ is a constant of proportionality fit to the data, SF is a value quantifying the shape of the beta-dispersion curve, and k is an offset value (which may be neglected in many cases). Other combinations of C and SF can be used besides this simple linear combination, which are readily ascertainable to those of ordinary skill in the relevant art.

Example Correction of Measured Permittivity at a Single Frequency by Correlating the Permittivity Response Over Multiple Frequencies to Measured Biological Properties FIG. 5 is a flow chart 500 that outlines an exemplary method of receiving measurements obtained by applying a frequency-varying signal to a population of cells with a measuring device, calculating divergences between the received electrical property measurements and a number of calibration measurements, and determining a relationship or correlation between the permittivity response as a function of the frequency varying signal and the divergence for generating a more accurate prediction of a viable cell volume for the population, as can be used in certain embodiments of the disclosed technology.

At process block 510, data representing a number of measurements of an electrical property of a population of cells are received. The measurements can be obtained by applying a frequency-varying signal (e.g., a sine wave having a frequency that is varied across a selected frequency range, or at two or more selected frequencies) to the population of cells while measuring an electrical property such as permittivity or capacitance. A number of selected frequencies can be used, for example, frequencies between 50 kHz and 10 MHz. The measured permittivity of the population of cells will vary depending on the frequency of the applied signal used to measure permittivity. For example, the permittivity can range from a high measurement of $4 \times 10^{-9}$ Farads per meter (F/m) at a low frequency of 50 kHz to a low measurement of $1 \times 10^{-11}$ F/m at a high frequency of 10 MHz. As used herein, the terms "low frequency" and "high frequency" are relative, and do not necessarily refer to an absolute low or high frequency. In this way, electrical property data as a function of frequency can be obtained. For example, the permittivity response as a function of frequency, such as the beta dispersion curve, can be measured.

The cells can be mammalian cells (e.g. from the CHO or NS0 cell lines) suspended in a nutrient solution.

The data collected at process block 510 can be collected over a period on the order of seconds, minutes, hours, or days, as is suited to the species of cells in the population and environmental conditions.

Figure 6A:
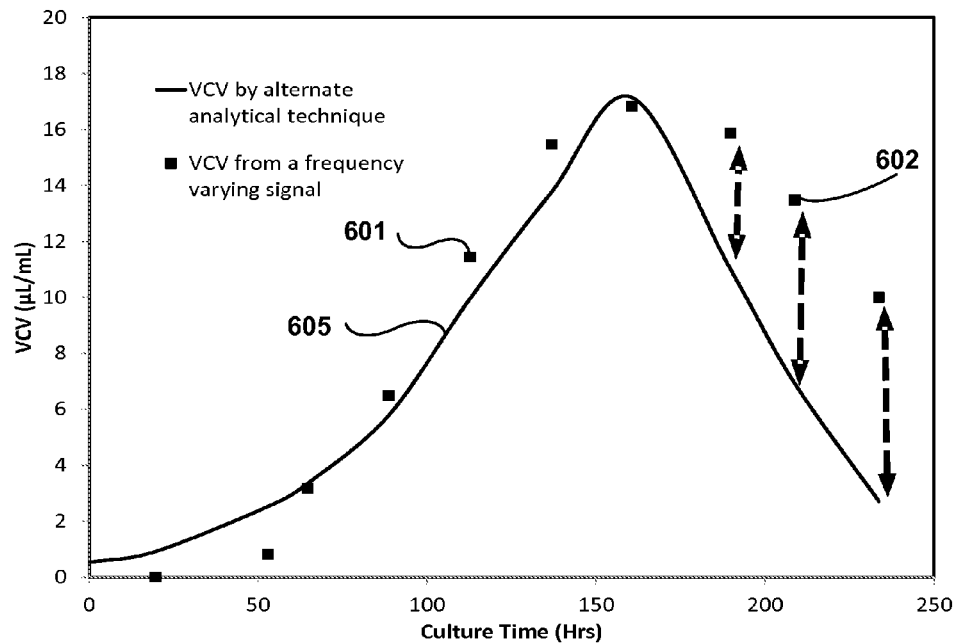
FIGS. 6A-B are charts illustrating experimental results obtained using exemplary methods of predicting viable cell volume obtained in accordance with the disclosed technology.

With certain cells, the predicted viable cell volume (VCV) of the population (as measured by the Aber Biomass Monitor 200 which determines VCV based on linear correlation between a measurement of the magnitude of the beta dispersion and the actual VCV measurements will begin to diverge from the actual VCV measured by trypan blue exclusion over the life cycle of the population, as illustrated in the chart 600 of FIG. 6A. FIG. 6A illustrates viable cell volume measured using the prior art probe and by Cedex, an automated cell counting device which uses trypan blue exclusion to determine VCV by image analysis. As shown, the permittivity probe VCV prediction is indicated by square sample points (e.g., points 601 and 602), and the VCV measured by trypan blue exclusion is indicated by a line 605. After measurement data using the alternate analytical technique (in this case trypan blue exclusion method) has been collected, the method proceeds to process block 520.

At process block 520, a calibration (in other words, a relationship) is calculated between the electrical property data as a function of frequency collected at process block 510 and measurements determined using an alternate analytical technique, in this case the trypan blue exclusion method. Certain cell populations exhibit a differing permittivity response for similar biomass volumes depending on the life cycle stage of the cells. Thus, the permittivity response as a function of frequency, or beta dispersion curve, can be used to identify the stage of the life cycle of the cell. For example, some cell populations exhibit differing permittivity responses before and after peak growth has been achieved.

In general, the term "alternate analytical techniques" refers to techniques for obtaining calibration measurements based on analyzing cell biomass in ways other than measuring at least one electrical property of a cell population by applying a frequency-varying signal to the cell population with a measuring device. Alternate analytical techniques suitable for performing such calibration measurements include, but are not limited to: enumeration using a hemocytometer, trypan blue exclusion, caspases for measuring cell apoptosis, fluorescence-activated cell sorting using flow cytometry, or other techniques known to one of ordinary skill in the art.

Figure 6B:
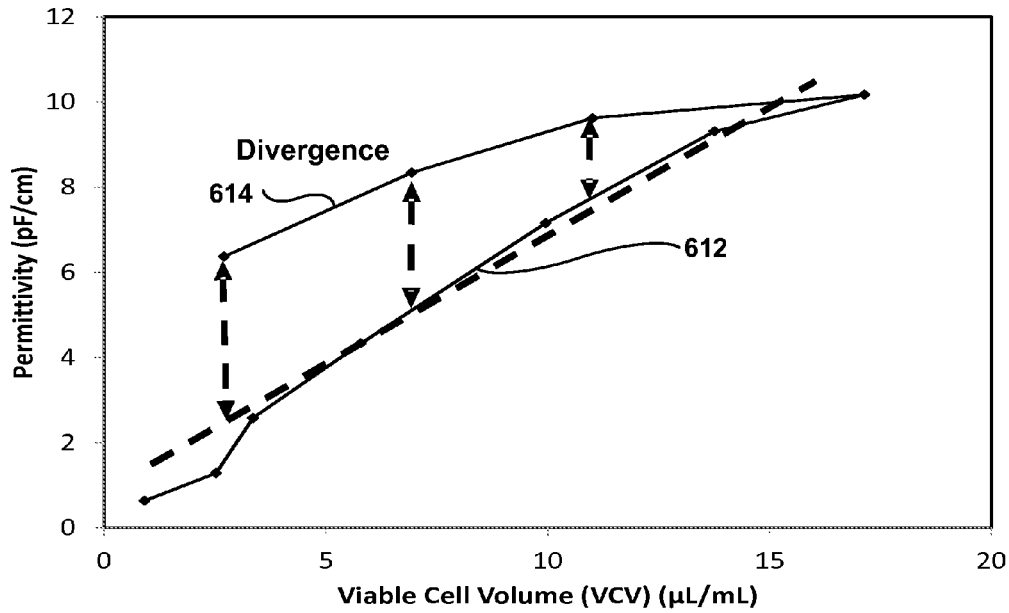

By comparing differences in permittivity response (as a function of frequency) as measured by an electrical measuring device applying a frequency varying-signal, to a measurement of biomass volume generated by an alternate analytical technique, a calibration (or relationship) can be calculated between the permittivity response and the actual biomass volume. FIG. 6B illustrates that the same viable cell volume will generate different permittivity values at a single frequency depending on the life cycle stage of the cells. In FIG. 6B, the permittivity measured at a single frequency is plotted against viable cell volume. FIG. 6B shows observed divergences between permittivities measured at a single frequency by the prior art probe during the growth phase of a culture (indicated by a first portion 612 of a data series), and permittivities measured during phases of stationary and decreasing viability phases (indicated by a second portion 614 of a data series), after peak biomass volume (here, after peak VCV) has been achieved. Such a divergence is typically caused by changes in the structure of the cell wall as the health of the cells in the culture decreases.

A calibration or relationship using the permittivity response as a function of frequency may be determined in order to improve the accuracy of future measurements of viable cell volume using the electrical property data. Turning to step 530 of FIG. 5, this is accomplished by characterizing the frequency dependence of the measured permittivity response by generating a value that is representative of the shape of the beta dispersion curve. A relationship is then determined between the frequency dependence of the permittivity response (that is, the value representative of the shape of the beta dispersion curve) and the viable cell volume as measured using the alternate analytical method, in this case the trypan blue exclusion method as measured by Cedex. In particular, the relationship is determined by correlating the value representative of the shape of the beta dispersion curve with the observed divergence between the magnitude of permittivity measured at a single frequency and the viable cell volume as measured using the alternate analytical method, in this case the trypan blue exclusion method as measured by Cedex. This relationship allows for the correction of the observed divergence between the viable cell volume as predicted by the prior art permittivity probe measured at a single frequency and the viable cell volume measured using trypan blue exclusion in future measurements of viable cell volume using only permittivity measurements. The calibration determined at process block 530 can then be used for measuring cell properties in other cell populations.

Example Method of Correlating Measurements to Alternate Calibration Measurements FIG. 7 is a flow chart 700 that outlines an exemplary method of correlating an area ratio based on permittivity measurements obtained using a permittivity probe to measurements obtained using an alternate analytical technique, as can be used in certain embodiments of the disclosed technology.

At process block 710, a number of permittivity measurements $\in$ are received that are obtained by applying a frequency-varying signal to a population of cells using a suitable measuring device. For example, a permittivity probe capable of applying a number of different frequencies to a suspension of cells in a bioreactor, such as the Futura line of biomass sensors and the Biomass Monitor 200 (manufactured by Aber Instruments of the United Kingdom), and the Fogale Biomass System (manufactured by Fogale Nanotech of France) can be used. Alternatively, suitable measuring devices include external electrodes placed on the outside or inside of the bioreactor and connected to an appropriate signal generator and receiver. Suitable frequencies and techniques for applying a frequency-varying signal to a population of cells as described above regarding process block 710 can be employed. An example of a number of permittivity measurements obtained by applying a frequency-varying signal using a permittivity probe are shown in chart 800 of FIG. 8A. As shown, four data series corresponding to measurements made at four different time periods (here, at days 3, 6, 8, and 11 of a cell population life cycle) are shown. As shown, the measured permittivity generally decreases as sampling signal frequency is increased, but each data series exhibits a different shape. That is, the permittivity response observed as a function of frequency is different for each of the different electrical property data series taken at the different time points.

Figure 8A:
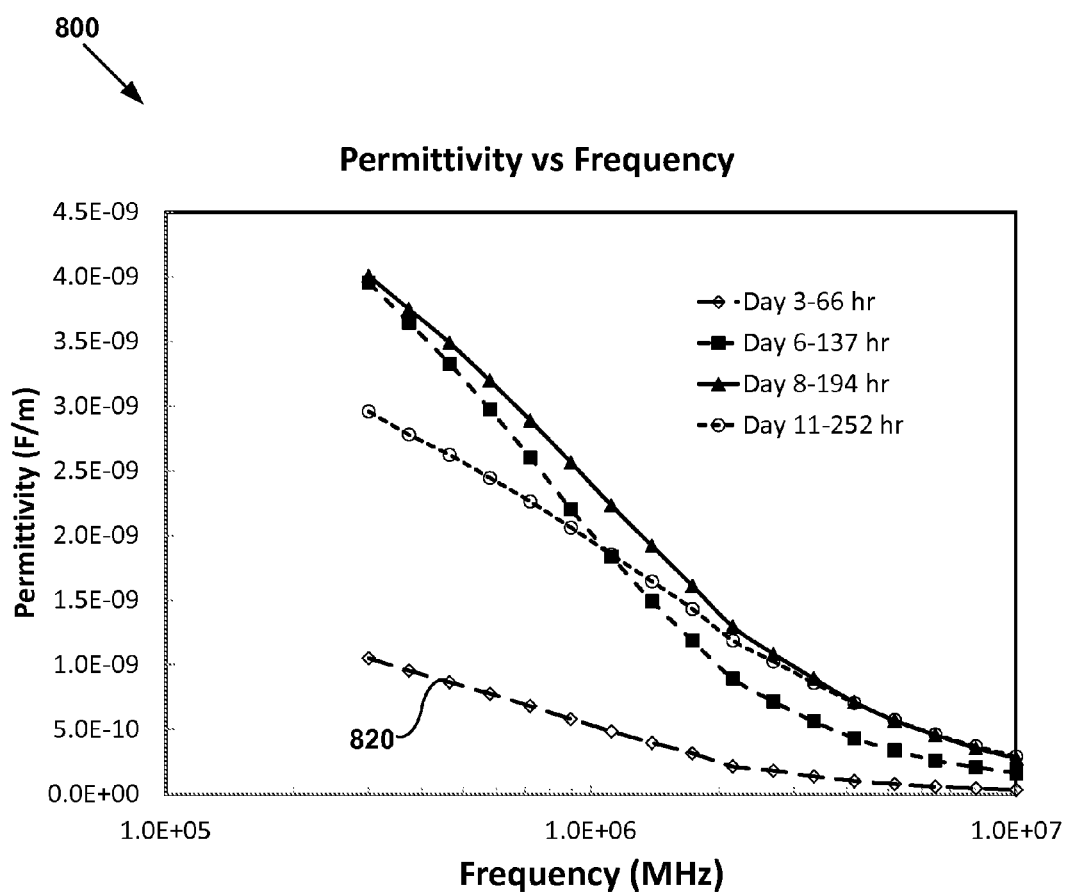
Figures 8B, 9:
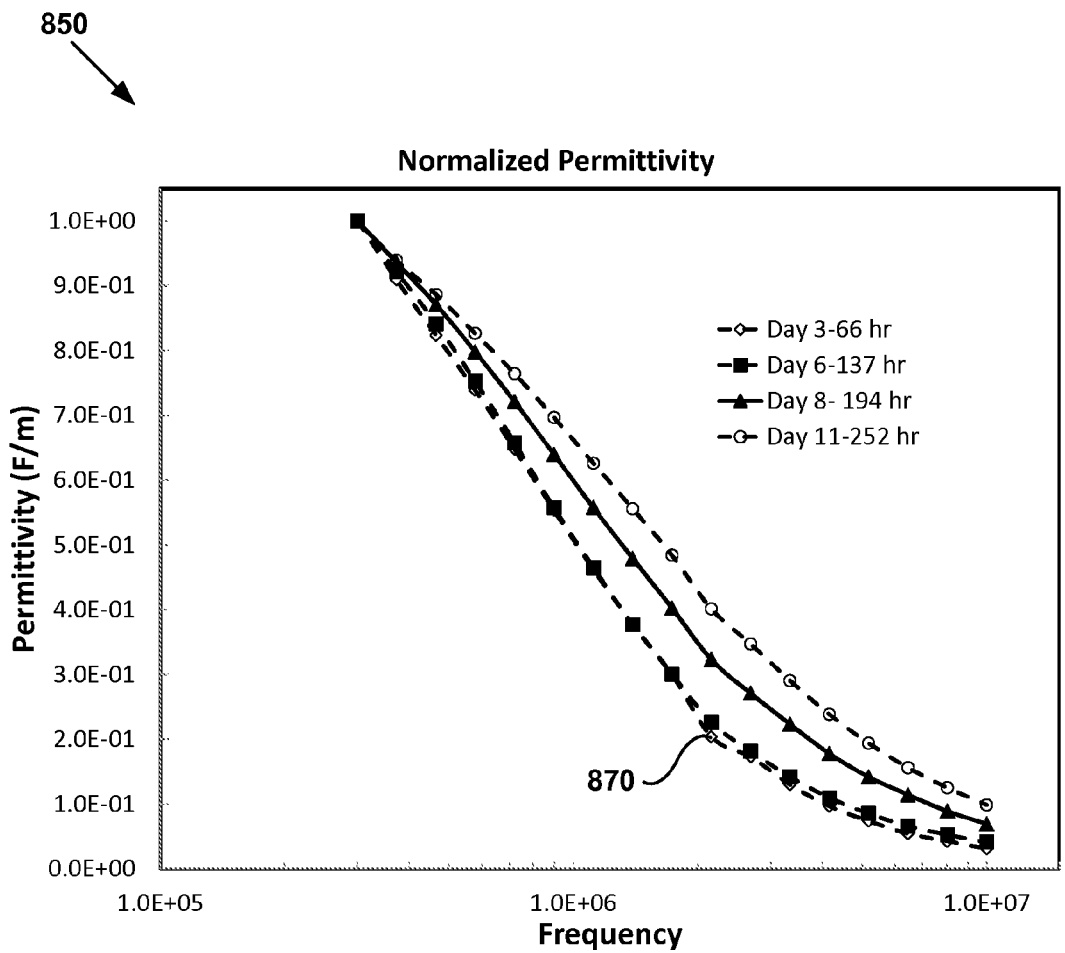
FIG. 8B is a graph illustrating a series of normalized permittivity versus frequency spectra taken at different time points.
FIG. 9 illustrates an exemplary equation for normalizing permittivity data.

The permittivity measurements $\in$ across all frequency spectra can be normalized to a range from 0.0 to 1.0 using the equation shown in FIG. 9. Thus, each permittivity measurement $\in$ is normalized by dividing by the maximum measured permittivity $\in_{max}$, for a set of measurements to produce a normalized permittivity $\in_N$. The normalized permittivity $\in_N$ will be used for determining area ratios $R_A$, as described below regarding process blocks 730-750. An example of four data series of normalized permittivity measurements $\in_N$ are shown in chart 850 of FIG. 8B. As shown, each of the four data series has been corrected to range from 0.0 to 1.0 (e.g., normalized data series 870 corresponds to data series 820 of FIG. 8A). The data series 820 was measured 66 hours into the life cycle of the cell culture. In other examples, the permittivity measurements are not normalized.

After obtaining a number of permittivity measurements and (optionally) normalizing the permittivity measurements, the method proceeds to process block 720.

At process block 720, a divergence is calculated between the permittivity measurements obtained at process block 710 and calibration measurements determined using an alternate analytical technique in a similar fashion to those described above regarding process block 520. For example, the divergence between the magnitude of the permittivity measured at a single frequency and the biological property measured using the alternate analytical technique (in this case viable cell volume) is calculated for each of the measured time points. After the divergence has been calculated, the method proceeds to process block 730.

Figures 10, 11, 12:
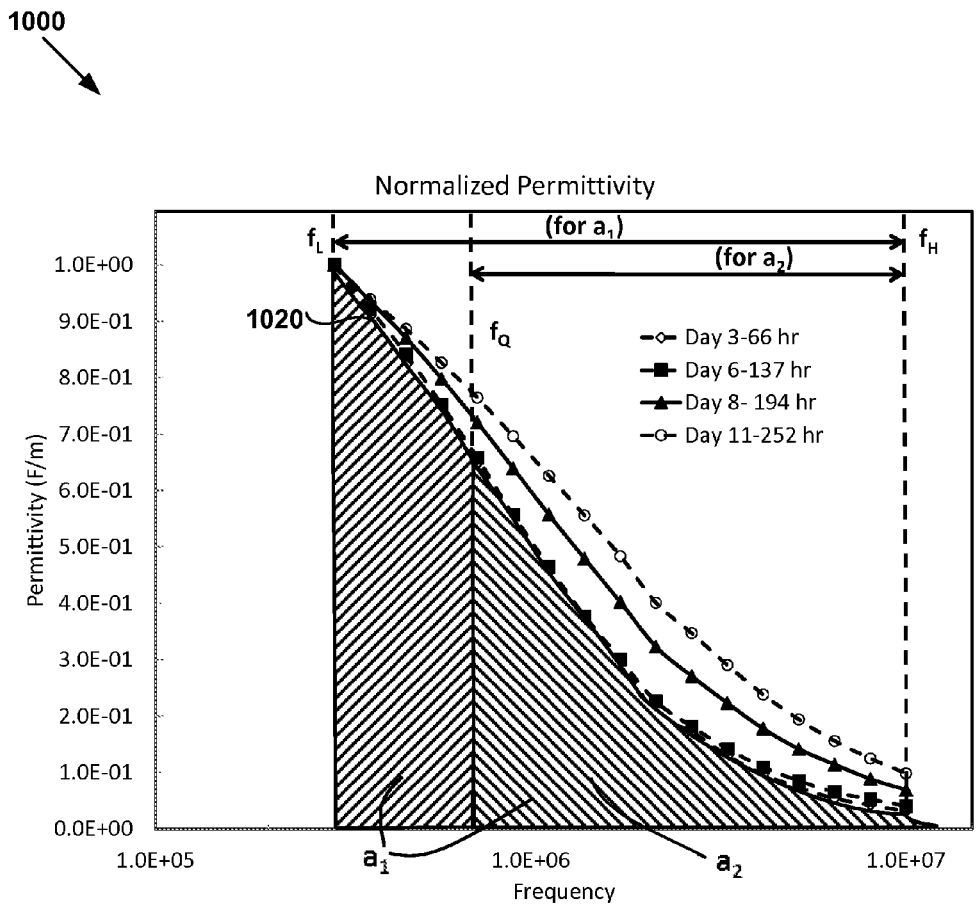
FIG. 10 is a graph illustrating generating a permittivity area ratio based on different frequency portions of one of the spectra from FIG. 8B.
FIGS. 11 and 12 illustrate exemplary equations for determining a permittivity area ratio using electrical property data.

In process blocks 730 to 750, a value representative of the permittivity response as a function of frequency, or shape of the electrical property data, is calculated using area ratios under the permittivity versus frequency curves. At process block 730, a first area $a_1$ is determined by integrating a number of permittivity measurements (or samples) taken between a selected low frequency $f_L$ and a selected high frequency $f_H$. In some examples, the highest and lowest frequencies are the highest and lowest frequencies applied to the population of cells when measuring permittivities. In other examples, other high and low frequencies are used as the selected frequencies. In some examples, the permittivity measurements are normalized, as discussed above regarding process block 710. The first area $a_1$ can be calculated using any suitable technique, including quadrature polynomial interpolation, adaptive quadrature interpolation, extrapolation, and/or Monte Carlo analysis. After calculating the first area $a_1$, the method proceeds to process block 740. For example, the chart 1000 of FIG. 10 shows this first area $a_1$ as first normalized data series 1020 for the range $f_L$ to $f_H$.

At process block 740, a second area $a_2$ is determined by integrating a number of permittivity measurements (or samples) taken between a selected frequency $f_Q$ and either the low frequency $f_L$ or the high frequency $f_H$ used for calculating the first area $a_1$ at process block 730. The frequency $f_Q$ is selected to be between $f_L$ and $f_H$. In some examples, the selected frequency is predetermined at a fixed frequency (e.g., 808.5 kHz) or as a proportion of the frequency (e.g., $f_Q$ is selected to include the upper three-fourths of the frequency range between $f_L$ and $f_H$). In other examples, the frequency $f_Q$ is selected based at least in part on the permittivity samples using a sensitivity analysis. For example, if the shape of a curve of the permittivity samples includes a "knee", or sharp change in the measured permittivity as a function of frequency (specifically in this case, an inflection point), the frequency point at the knee is used as the selected frequency $f_Q$ as an appropriate region to correct for unhealthy cells in the population. In other examples, an inflection point along the curve of the permittivity samples is used as the selected frequency $f_Q$. In other examples, the frequency $f_Q$ is selected based on previously-measured permittivity data. Integration of the area underneath the curve formed by the permittivity samples can be performed in a similar manner as described regarding process block 740. For example, the chart 1000 of FIG. 10 depicts this second area $a_2$ for the first normalized data series 1020 for the range $f_Q$ to $f_H$. As shown in FIG. 10, the first area $a_1$ comprises all of the area of the second area $a_2$, as well as additional area to the left of $f_Q$. After calculating the second area $a_2$, the method proceeds to process block 750.

At process block 750, an area ratio $R_A$ is calculated. The area ratio $R_A$ is a value that is representative of the shape of the permittivity versus frequency curves shown in FIG. 10. For example, the second area $a_2$ divided by the first area $a_1$ is used as the area ratio $R_A$. An example equation for calculating the area ratio $R_A$ for an integral between a selected frequency $f_Q$ and a high frequency $f_H$ is shown in FIG. 11. An example equation for calculating the area ratio $R_A$ for an integral between a low frequency $f_L$ and a selected frequency $f_Q$ is shown in FIG. 12. Other area ratio calculations can be used. An area ratio $R_A$ can be calculated for each set of permittivity measurements obtained at a particular point in time. For example, data for permittivity measurements might be obtained every 12 hours for a cell population over a period of 10 days, and a corresponding area ratio $R_A$ is calculated for each set of frequency-swept permittivity measurements. After a number of area ratios $R_A$ are calculated, the method proceeds to process block 760.

At process block 760, a number of area ratios $R_A$ calculated at process block 750 are correlated to calibration measurements determined using the alternate analytical technique at process block 720. For example, viable cell volume (VCV), measured using an automated cell counter (e.g., a Cedex analyzer), can be used to automatically count cells to determine VCV using typan blue exclusion. As will be readily understood to one of ordinary skill in the art, any of a number of suitable alternate analytical techniques can be used. Further, the calibration measurements are not limited to VCV, but in some examples can include other biomass properties such as packed viable cell volume (PVCV), viable cell density (VCD), viable cell concentration (VCC), viability, cell health, level of apoptosis, or other suitable measurements. The correlation can be calculated using a suitable technique, including linear correlation methods (e.g., using Pearson's linear correlation), non-linear correlation (e.g., using Spearman's rank correlation), or matrix correlation techniques. Thus, in some examples, a correlation in slope-intercept form is calculated, while in other examples, more complex correlations are used. The correlations thus calculated can be used to correct divergences observed in other cell cultures using permittivity measurements, or measurements of other suitable electrical properties. That is, the viable cell volume predicted using the magnitude of the permittivity measured at frequency $f_c$ can be corrected using the correlation between the area ratio and the divergence to correct the viable cell volume predicted using only the magnitude of the measured permittivity.

FIG. 13A includes a chart 1360 that illustrates a number of measurements and calculations over a culture time of 250 hours based on performing the exemplary method of FIG. 7. As shown, a line 1361 indicates the calculated area ratios for the upper three-fourths of frequencies (as shown, above 808.5 kHz). A number of sample points (e.g., sample points 1362 and 1363) indicate cell viability (as measured using a Cedex analyzer). A line 1364 indicates predicted viability calculated using area ratios based on frequencies above 808.5 kHz using the method described in FIG. 7.

FIG. 13B includes a chart 1370 that depicts a corresponding correlation 1371 generated between area ratios for the upper three-fourths of frequencies (as shown, area ratios calculated for frequencies above 808.5 kHz) and percent cell viability (as measured using a Cedex analyzer). Thus, as shown, values representative of the shape of the electrical property data (the area ratios under the permittivity versus frequency curves) can be correlated to the biological property (percent viability) measured using an alternate analytical technique. The electrical property measurements made using a frequency-swept measuring device can be used to form a fit to biological property data obtained using alternate analytical techniques, and the resulting correlation can be used in subsequent measurements to obtain more accurate predictions of the biological property.

Example Method of Predicting Viable Cell Volume Using Area Ratio Correlation

FIG. 14 is a flow chart 1400 illustrating an example of receiving a first set of electrical property measurements for a population of cells and applying a correlation to the first set of measurements to generate a prediction of cell viability, as can be used in some examples of the disclosed technology.

At process block 1410, a first set of electrical property measurements (or samples) are received, the measurements being obtained from applying a frequency-varying signal to a first population of cells with a measuring device. For example, a permittivity probe can be used to measure permittivity or capacitance of the first population when applying a frequency-varying signal using similar techniques to those described above regarding process block 510. Suitable electrical properties that can be measured with a measuring device include capacitance, permittivity, dielectric constant, resistance, impedance, voltage, or current. After obtaining the first set of measurements, the method proceeds to process block 1420.

At process block 1420, a correlation is received based on a second set of electrical property measurements for a second set of cells. For example, the correlation can be determined using the techniques described above regarding FIG. 7. Thus, the received correlation describes the relationship between an electrical property of the cell population and measurements of cell biomass, such as VCV, PVCV, VCD, VCC, viability, cell health, or level of apoptosis. After the correlation is received, the method proceeds to process block 1430.

At process block 1430, the correlation received at process block 1420 is applied to generate one or more corrected measurements based on the first set of measurements received at process block 1410. For example, if the correlation is in the form of a slope-intercept equation, the equation can be used to calculate corrected measurements based on normalized permittivities based on the first set of electrical property measurements. Thus, a more accurate measurement of cell state can be obtained in the first population, without the use of the alternate analytical technique(s) used to produce the correlation.

Further Detailed Example of Predicting Viable Cell Volume

Figure 15B:
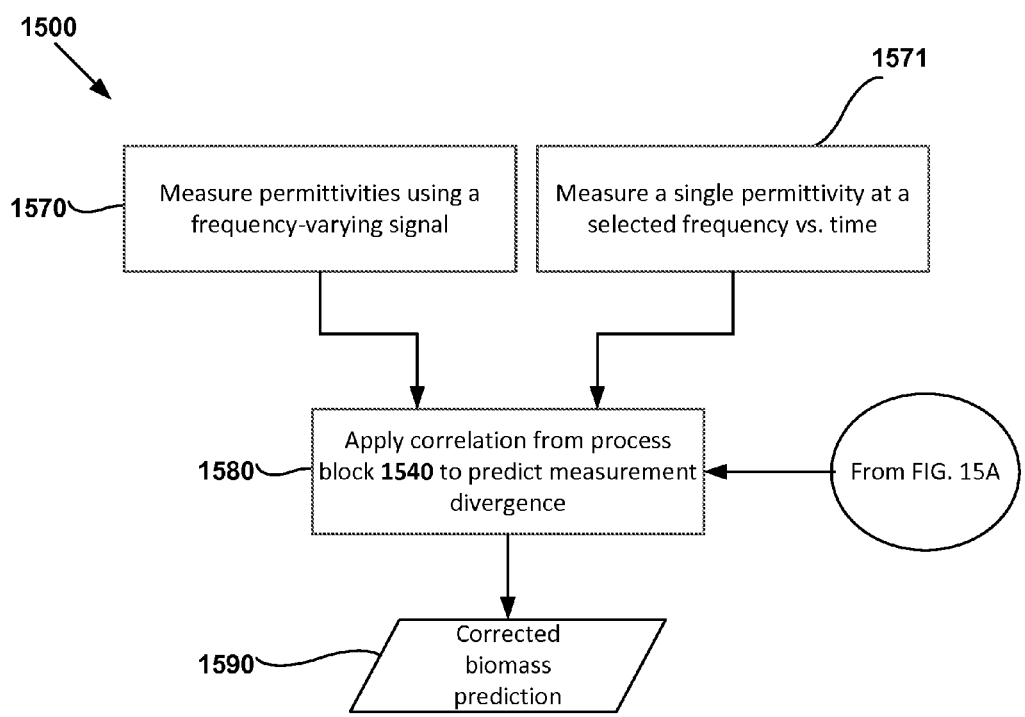

FIGS. 15A-15B illustrate a flow chart 1500 outlining another, further detailed, example of predicting divergence of electrical properties for a population of cells to correct cell viability predictions, as can be used with certain examples of the disclosed technology. Charts depicting data associated with an example population of cells analyzed using the exemplary method depicted in the flow chart 1500 are shown in FIGS. 6A and 6B, FIGS. 8A and 8B, FIG. 10, FIGS. 13A and 13B, and FIGS. 16A-E. These charts are not limited to this example method, however, and also can be used to illustrate other embodiments of the disclosed technology.

At process block 1510, permittivity of a first population of cells is measured at one or more selected frequencies over a period of time. For example, a permittivity probe can be used to measure the capacitance at multiple frequencies during the life cycle of a population of mammalian cells, in a similar fashion to that described above regarding process block 210. In other examples, a capacitance, or other electrical property, of a population of cells can be measured at one or more selected frequencies over a period of time.

At process block 1511, a number of viable cell volume measurements are measured offline for a second population of cells over a period of time using an alternate analytical method. For example, a similar population of cells of the same species as measured at process block 1510 can be measured using trypan blue exclusion or other methods previously mentioned. The measurements made at process block 1510 and 1511 need not occur during the same time period. For example, the viable cell volume measurements can be performed weeks or months before the capacitance measurements made at process block 1510. After measuring the capacitances and viable cell volumes at process block 1510 and 1511, the method proceeds to process block 1520.

At process block 1520, permittivity data (e.g., based on the capacitance measured at process block 1510) are received (e.g., at a suitable computing environment). The capacitance values measured at process block 1510 can be expressed as capacitance, permittivity, or other suitable electrical property. The permittivity data can be normalized before being received, or received in absolute or relative values and normalized using the computing environment. After receiving the permittivity data, the method proceeds to process block 1530.

At process block 1530, the received permittivity data based on the measured capacitances from process block 1510 are compared to the viable cell volume data measured at process block 1511. As shown in FIG. 16A, a chart 1650 of the permittivities at a single frequency (expressed in pF per cm) can be plotted along a y-axis vs. viable cell volumes (expressed in μL per mL) along an x-axis, where the viable cell volumes are measured using the alternate analytical method at process block 1511. As shown, a lower portion 1651 of the charted permittivities represents measurements taken during the growth phase of the population of cells, while the upper portion 1652 represents measurements taken after the growth phase. Thus, FIG. 16A depicts a clear divergence of permittivity vs. viable cell volume based on the life cycle of the cells in the population.

Figure 16C:
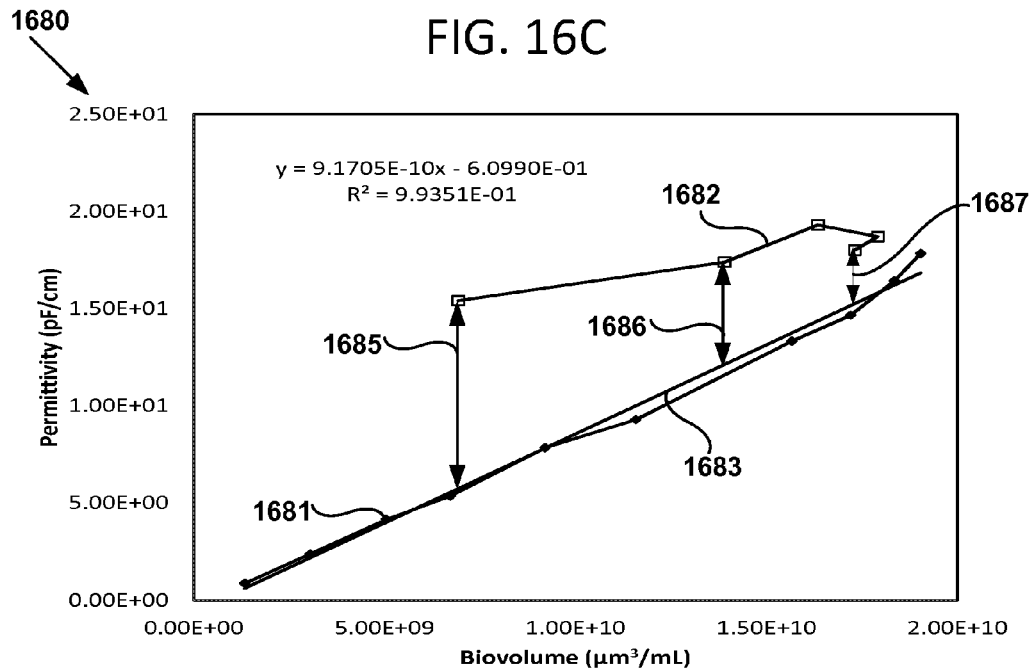
Figure 16D:
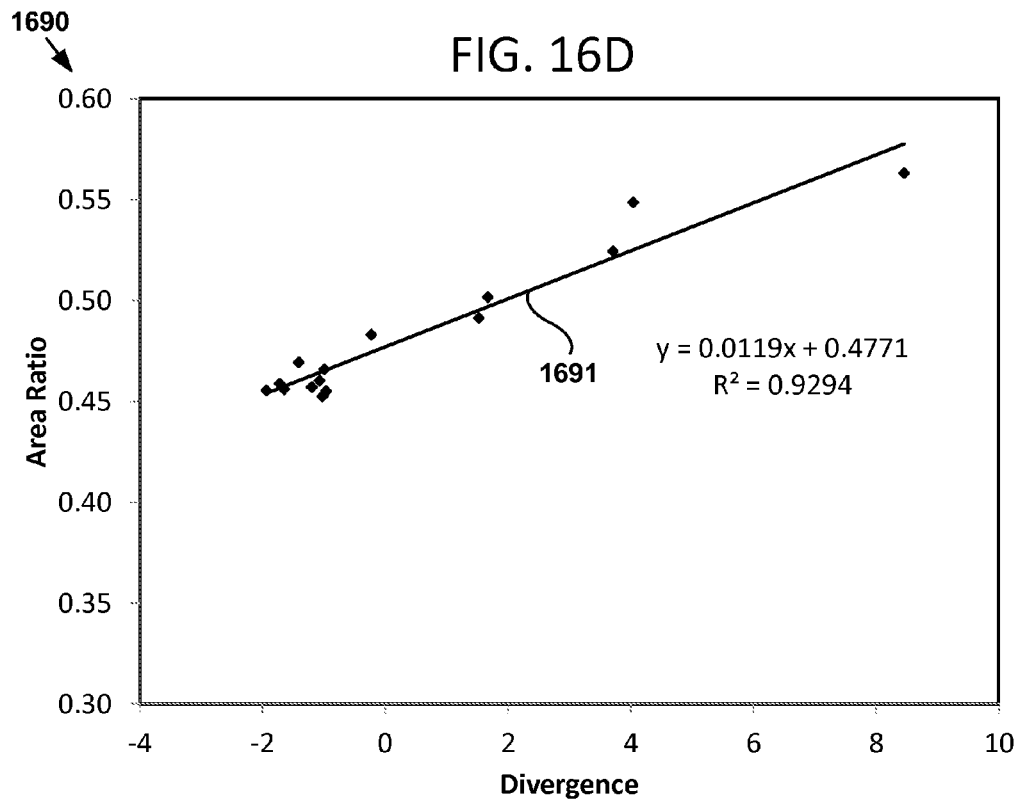

At process block 1532, one or more "healthy" points on the permittivity plot are selected to develop a linear correlation vs. capacitance. The healthy points are selected as the points that correspond to the growth phase of the culture. The healthy points can be selected in a number of ways. For example, a person can analyze the data and select the healthy points. Alternatively, the healthy points can be detected by comparing previously-measured permittivities. For example, when permittivity begins to fall, the growth phase is determined to have passed, and only previous permittivity samples are considered. In other examples, the healthy points can be determined based on when the viable cell volume measurements from process block 1511 begin to decrease. As shown in FIG. 16C, a data point 1681 in the lower portion of the data series has been determined to be a healthy point during the growth phase, while another data point 1682 of the data series has been determined to be a measurement taken after the peak viable cell volume has been achieved in the first population of cells. After a linear correlation is generated for the healthy points (represented in FIG. 16C as a line 1683), the method proceeds to process block 1534.

At process block 1534, the divergence (e.g., the divergences indicated by arrows 1685, 1686, and 1687 in FIG. 16C) of each measurement from the linear correlation generated at process block 1532 is calculated. In some examples, the divergences can be filtered to select non-healthy points, by only keeping divergences above a certain absolute or percentage threshold. In other examples, all the divergences are kept for later correlation. After calculating the divergences of one or more samples from the linear correlation, the method proceeds to process block 1540.

At process block 1540, the divergences calculated at process block 1534 are correlated with an area ratio to produce a correlation for use with subsequent analyses of cell populations. That is, the divergences are correlated with a value representative of the shape of the beta dispersion curve corresponding to the respective time point at which the permittivity was measured. For example, the area ratios can be calculated in a similar fashion as the area ratios discussed above regarding FIG. 7. An example of a correlation between area ratios in the upper three-quarters of the frequency spectrum used to measure the population of cells, and the divergences calculated at process block 1534, is shown in the chart 1690 of FIG. 16D. As shown, the divergences exhibit a nearly linear correlation (represented by a line 1691) to the selected area ratios. Thus, a relationship is established between the area ratios, or value representative of the shape of the permittivity versus frequency data, and the biological property data measured by the alternate analytical technique, in this case based on the divergences between the biological property data measured by the alternate analytical technique and permittivity measured at a single frequency.

This correlation between the area ratios and the divergence between magnitude of the permittivity data and the actual viable cell volume can be used for subsequent runs for similar cells in order to correct the viable cell volume predicted by permittivity values only, especially after growth phases, where greater divergences are observed between the viable cell volume predicted by the magnitude of the permittivity and the actual cell volume as measured by the trypan blue exclusion method. The correlation can be stored in a computer-readable storage media for use by, for example, a computing environment coupled to a bioreactor control system, or, alternatively, the correlation can be stored on computer-readable storage media in a computing cloud, for example, at a website hosted by a probe manufacturer or cell line provider.

FIG. 15B illustrates an additional technique that can be performed once the correlation has been generated at process block 1540. The techniques associated with process blocks 1570-1580 can be performed by a different entity than the one performing the method associated with process blocks 1510-1540, or by the same entity.

At process block 1570 capacitances (or, alternatively, permittivities) for a second population of cells are measured at two or more selected frequencies over a number of periods of time. For example, a permittivity probe can be used to measure the capacitance at multiple frequencies during the life cycle of a population of mammalian cells, in a similar fashion to that described above regarding process block 510. In some examples, the selected frequencies and/or time periods are the same as those used for the measurements made at process block 1510, while in other examples, the selected frequencies and/or time periods are different.

At process block 1571, a permittivity at a single selected frequency is measured for the second population of cells (which is indicative of the magnitude of the beta-dispersion). The viable cell volume predicted by this permittivity measurement is corrected based on the permittivities measured using the frequency varying signal at process block 1570. The change in shape of the permittivity vs. frequency curve indicates a time where the permittivity to viable cell volume relationship begins to diverge. After the permittivities have been measured at process blocks 1570 and 1571, the method proceeds to process block 1580.

At process block 1580, the correlation generated at process block 1540 is applied to calculate a divergence of the measurements made at process blocks 1570 and/or 1571 from the correlation. Thus, by using this correlation, the prediction of viable cell volume based on permittivity measurements made at process blocks 1570 and/or 1571 can be corrected, without using alternate analytical methods.

Figure 16E:
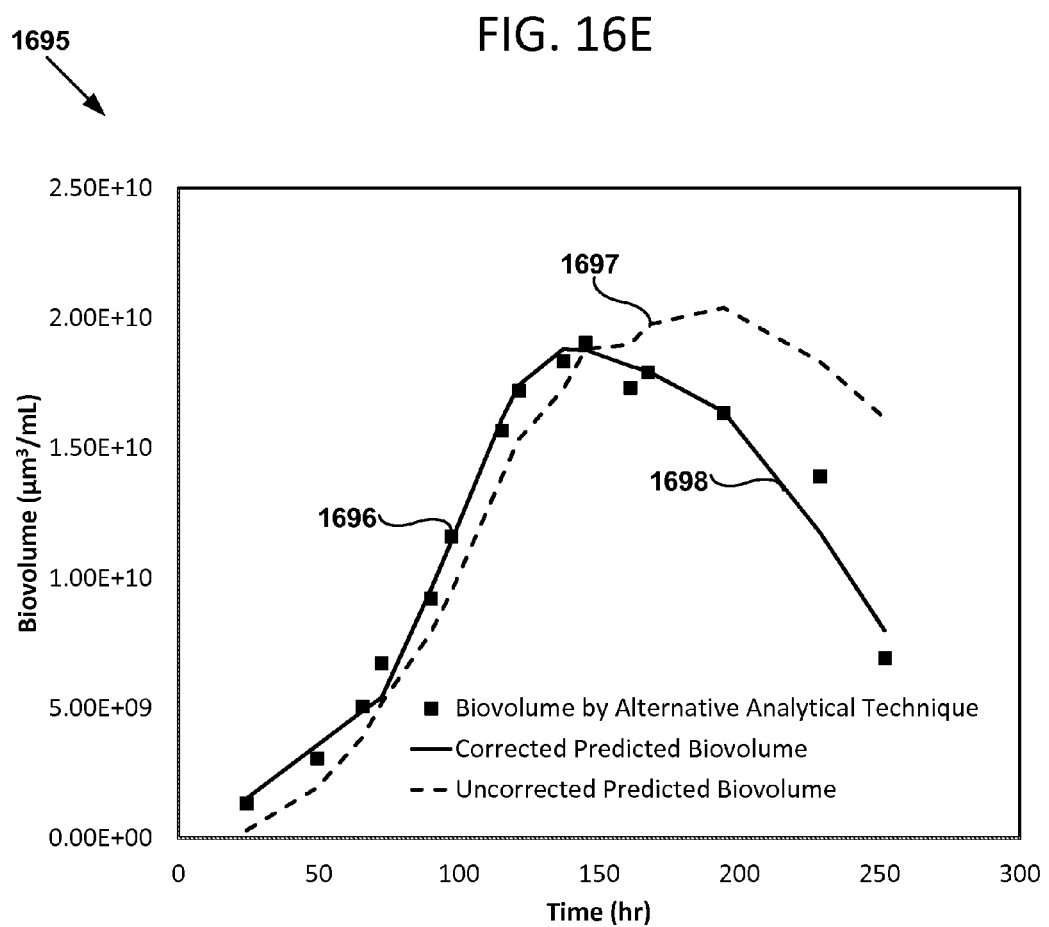

Once divergences have been calculated, attributes of the second population of cells, such as viable cell volume (VCV), packed viable cell volume (PVCV), viable cell density (VCD), viable cell concentration (VCC), viability, cell health, or level of apoptosis can be predicted. A chart 1695 of FIG. 16E shows an example of the biovolume (e.g., data point 1696) as measured by a Cedex analyzer (using trypan blue exclusion), the uncorrected predicted biovolume (e.g., data series 1697) as measured by a permittivity probe, and the corrected predicted biovolume (e.g., data series 1698) based on the techniques described above.

Example Method of Growing Cell Culture Using a Cell Biomass Prediction

FIG. 17 is a flow chart illustrating an example of growing cells in a conductive medium, receiving a biomass (e.g., VCV) prediction based on a correlation between two measurement techniques, including applying a frequency varying signal to the conductive medium, and adjusting conditions of the conductive medium based on the cell viability prediction.

At process block 1710, a population of cells is grown in a conductive medium, using, for example, the bioreactor system 100 described above regarding FIG. 1. The cells can be grown in an aseptic environment in communication with a permittivity probe at least partially immersed in the population. In other embodiments, the probe can be immersed or otherwise interact with the population for only limited durations of time. After the cell environment is configured as desired for cell growth, the method proceeds to process block 1720.

At process block 1720, a corrected prediction of cell biomass (e.g., VCV) is received based on a correlation of two measurement techniques. For example, the technique of applying a frequency varying signal to the conductive medium of process block 1710 can be used as the first technique for one of the measurements, and an offline measurement technique, such as trypan blue exclusion, can be used as the second measurement technique. The correlation can be linear or nonlinear, and can be based on the techniques discussed above regarding FIGS. 2, 7 and 15A-B. The prediction can be generated locally (e.g., by a control system having a computing environment) or remotely (e.g., in a computing cloud). After a prediction of cell biomass is received, the method proceeds to process block 1730.

At process block 1730, one or more environmental conditions of the population of cells are adjusted based on the prediction of cell biomass generated at process block 1720. For example, feeding media, water, acid or base solutions, or other inputs can be increased, decreased, withheld, or added. Other inputs can also be adjusted, such as the temperature of the bioreactor or agitation of the cell population. Outputs from the bioreactor can also be adjusted. For example, a sample of cells from the cell population can be acquired, or a determined fraction of the cell population volume removed from the bioreactor. The inputs and/or outputs can be selected for example, to improve the rate of cell growth, to improve cell health, or to retard or stop cell growth. Thus, a bioproduct can be produced based on the correlation of the first measurement technique to the second measurement technique.

Example Method of Using Frequency-Varying Signals and Calibration Measurements to Measure Apoptosis Apoptosis (programmed cell death) is a highly-regulated, well-defined biological process. Apoptosis leads to characteristic changes in cell morphology and cell death, for example, blebbing, cell shrinking, and nuclear fragmentation. Apoptosis is essential for multicellular life, and defects in the apoptosis process can lead to fatal diseases such as cancer.

Detection and measurement of apoptosis is useful for a number of reasons. For example, dead cells do not produce proteins or other byproducts as living cells do. Some of the causes of apoptosis are well-understood to those of ordinary skill in the art. For example, nutrient deprivation, waste accumulation, and process conditions, including oxidative stress, hypoxia, and shear, are causes of apoptosis.

Table 2 lists a number of stain targets, along with a corresponding apoptosis phase for detecting the stain targets.

TABLE 2

| Stain Target | Apoptosis Phase |
|---|---|
| DNA | Very late (dead) |
| Caspase 3 | Middle |
| Caspase 6 | Middle |
| Caspase 9 | Middle |
| Phosphatidyl-serine | Early |

FIG. 18 is a flow chart 1800 that outlines an exemplary method of receiving electrical measurements obtained by applying a frequency-varying signal to two different population of cells with a measuring device, one of the populations being grown in an apoptosis-induced environment, and predicting the level of apoptosis in one of the populations, as can be used in certain embodiments of the disclosed technology.

Figure 19A:
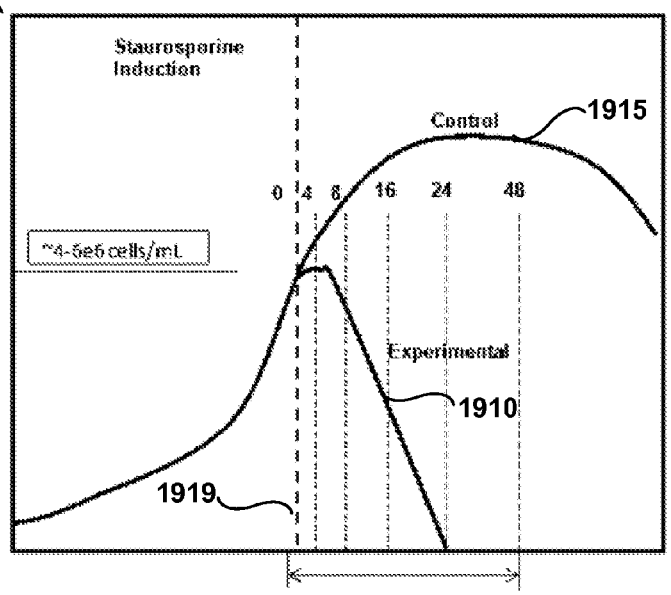

FIG. 19A is a chart 1900 that illustrates the viability of cells (along the y-axis) in two different cell populations over a period of time (along the x-axis) in an example experiment corresponding to the method of FIG. 18. As shown, a first line 1910 indicates the viability of a first population of cells, which has apoptosis induced using addition of a staurosporine agent. In this case, a 1 μM concentration of staurosporine was used. A second line 1915 indicates the viability of a second population of cells, which is a control population that is not induced using a staurosporine agent.

At process block 1810, data representing a number of measurements of an electrical property of a first population of cells are received. The measurements can be obtained by applying a frequency-varying signal (e.g., a sine wave having a frequency that is varied across a selected frequency range, or at two or more selected frequencies) to the population of cells while measuring an electrical property such as permittivity or capacitance. A number of selected frequencies can be used, for example, frequencies between 50 kHz and 10 MHz. The measured permittivity of the population of cells will vary depending on the frequency of the applied signal used to measure permittivity. For example, the permittivity can range from a high measurement of $4 \times 10^{-9}$ Farads per meter (F/m) at a low frequency of 50 kHz to a low measurement of $1 \times 10^{-11}$ F/m at a high frequency of 10 MHz. As used herein, the terms "low frequency" and "high frequency" are relative, and do not necessarily refer to an absolute low or high frequency. The cells can be mammalian cells (e.g. from the CHO or NS0 cell lines) suspended in a nutrient solution.

The data collected at process block 1810 can be collected over a period on the order of seconds, minutes, hours, or days, as is suited to the species of cells in the population and environmental conditions. As shown in the chart 850 of FIG. 8B, the normalized permittivity (plotted on the y-axis) of the population of cells is measured at a number of different frequencies (plotted on the x-axis) at the following time periods after initiation of cell growth: day 3, day 6, day 8, and day 11 (870). The shape of the curve thus obtained shifts over time, due to changes in the cellular structure of the cell population.

At a designated time period, apoptosis is induced in the first population of cells by adding an apoptosis inducing agent to the environment. For example, as shown in FIG. 19A, apoptosis is induced in the first population of cells at a time indicated by a dashed line 1919.

At process block 1820, a second set of measurements of an electrical property for a second population of cells is received using similar techniques to those discussed regarding process block 1810. The second population of cells has differing environmental conditions than those used for the first population of cells at process block 1810. For example, the second population of cells can be a control population, that does not have apoptosis induced using an agent. The second line 1915 indicates the viability of the control population.

Figure 19B:
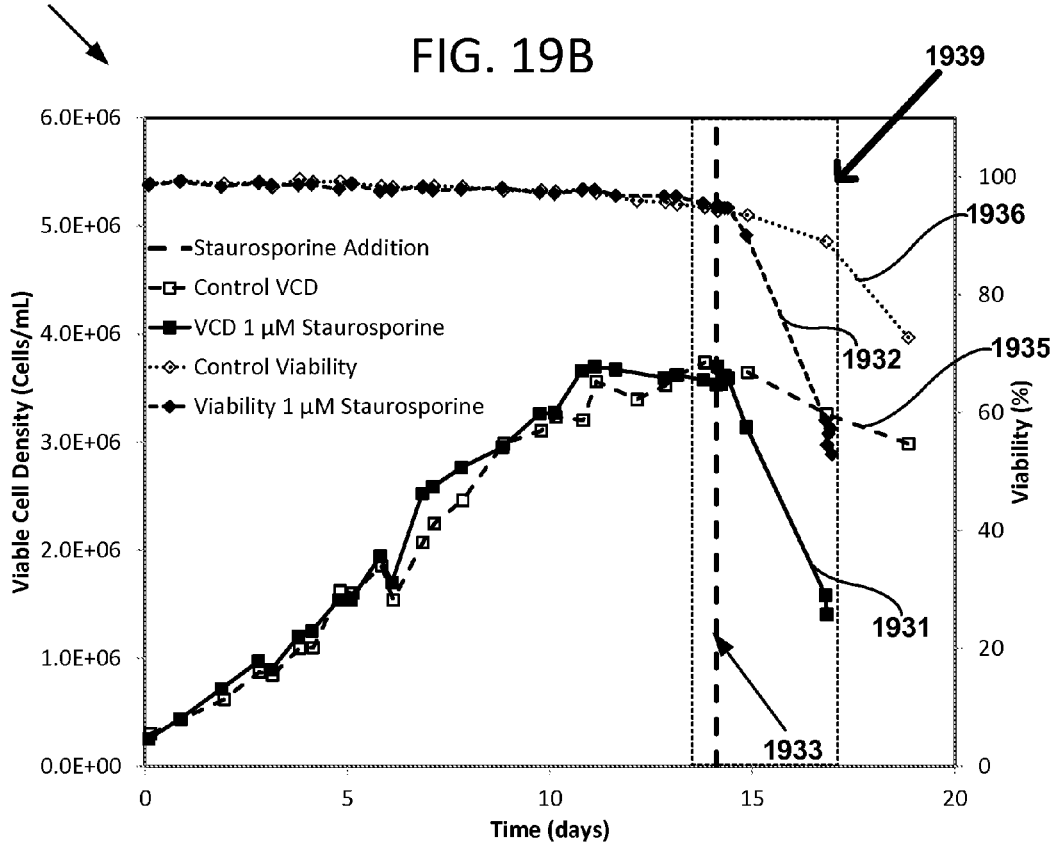
Figure 19C:
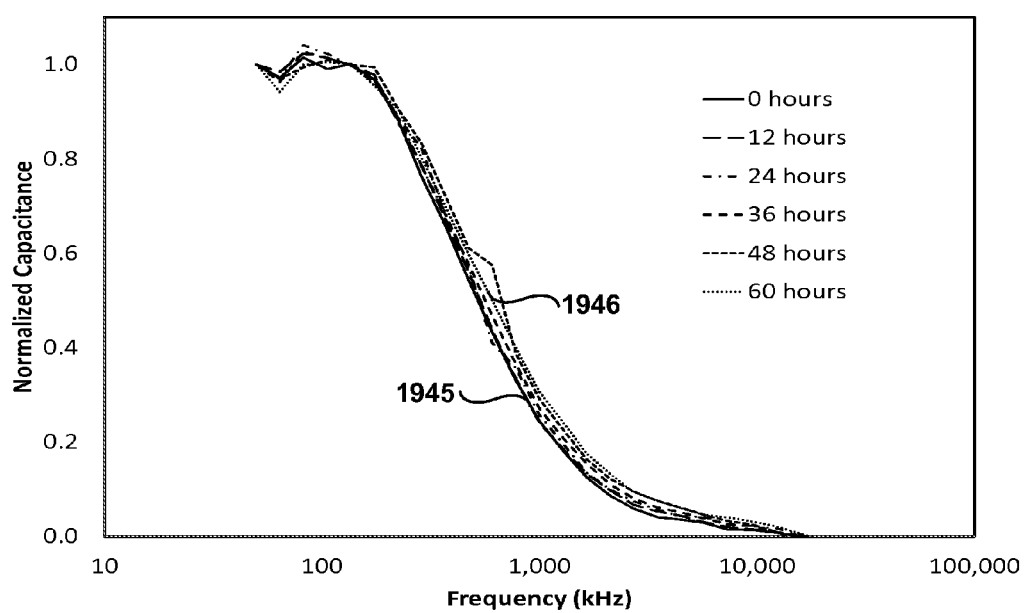

FIG. 19B is a chart 1930 that illustrates viable cell density (VCD) (left y-axis) and cell viability percentage (right y-axis) plotted over time (x-axis) for the first and second measurements of the first and second populations of cells received at process block 1810 and 1820. As shown in FIG. 19B, the first population of cells that is treated with staurosporine at day 14 (at a time 1933 indicated by a dashed line) exhibits declining VCD (data series 1931) and viability percentage (data series 1932). The untreated second population of cells exhibits declining VCD (data series 1935) and viability percentage (data series 1936), but at a substantially reduced rate of decline. A dashed box 1939 indicates the time period of FIG. 19B that is illustrated in more detail in FIGS. 19C-G.

At process block 1830, the first set of measurements for the first population of cells and the second set of measurements for the second population of cells are compared. As shown in the chart 1940 of FIG. 19C, a number of normalized capacitance measurements (on the y-axis) for the second set of measurements received at process block 1820 are plotted against the frequency at which the measurements were obtained (x-axis), respectively. A slight drift to the right is observed from measurements obtained at time 1933 (line 1945) and after 60 hours of cell growth (line 1946) after time 1933.

Figure 19D:
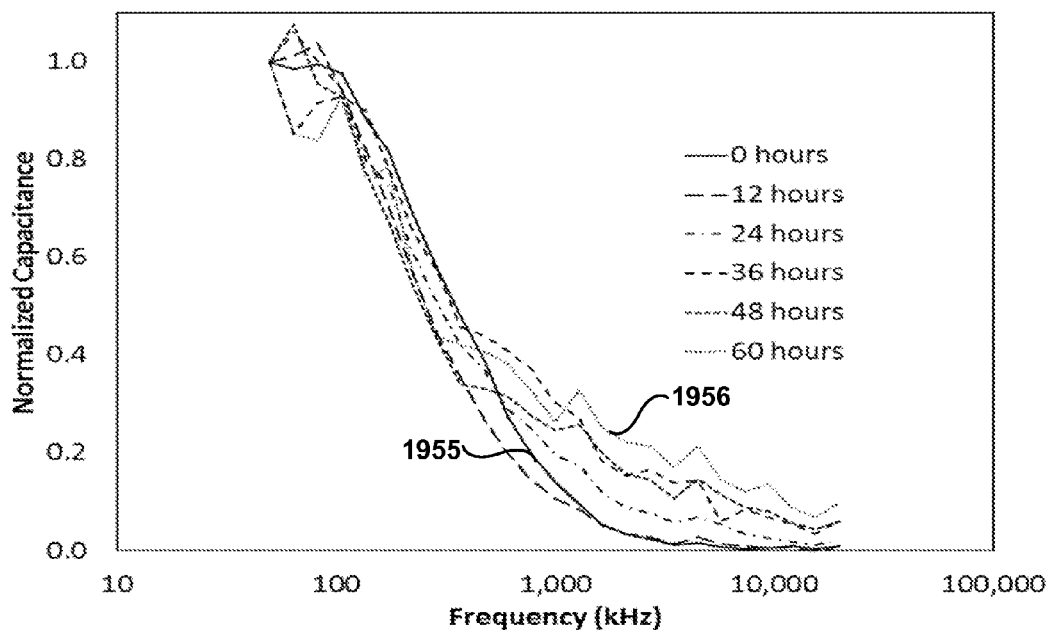

The chart 1950 of FIG. 19D illustrates the first set of measurements obtained from the first population of cells that has an apoptosis-inducing agent added at day 14 of cell growth. As shown, a more substantial drift to the right is observed from measurements (line 1955) obtained at the time 1933 of adding staurosporine cell growth to 60 hours after the staurosporine addition (line 1956).

Figure 20A:
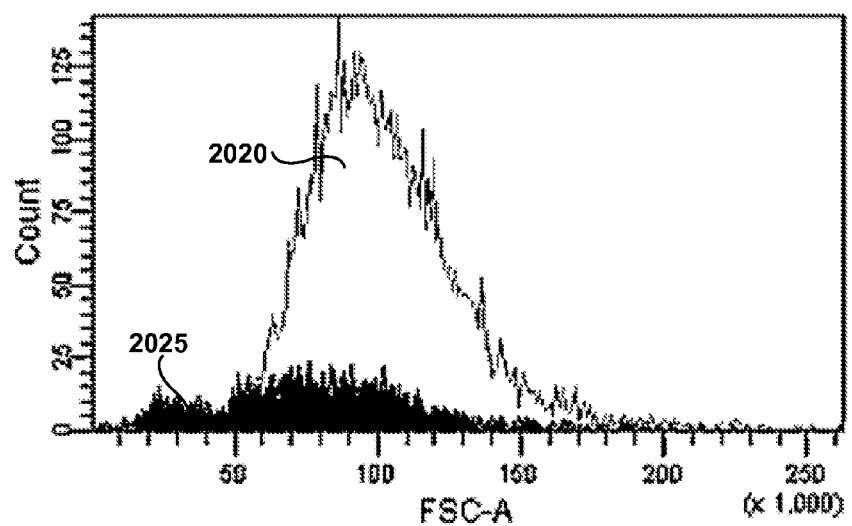
FIGS. 20A and B are graphs illustrating various measurements obtained over time for cell populations as can be observed using the method outlined in FIG. 18.
Figure 20B:
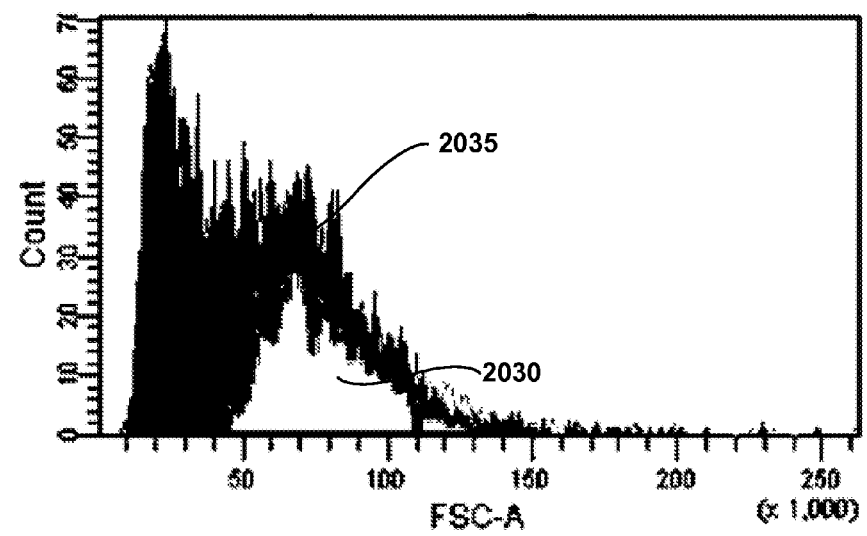

At process block 1840, a predicted level of apoptosis is generated based on viability measurements obtained using an alternative method. For example, a correlation to viability measurements obtained using staining techniques can be used. FIGS. 20A and 20B are charts 2000 and 2010 of histograms of cell counts (y-axis) plotted against FSC (forward scattering) measurements obtained using a flow cytometer at day 2 and day 10 of cell growth of the first population of apoptosis induced cells, respectively.

As shown in FIG. 20A, a first histogram 2020 indicates the population of healthy cells and a second histogram 2025 indicates the population of unhealthy cells, as determined by measuring FCS using a flow cytometer after 48 hours of cell growth in the first population of cells (before inducing apoptosis). As shown in FIG. 20B, a third histogram 2030 indicates the population of healthy cells and a fourth histogram 2035 indicates the population of unhealthy cells, as determined by measuring FCS using a flow cytometer after 10 days of cell growth in the first population of cells.

By comparing differences in permittivity response of a measuring device to a prediction of biomass volume generated by an alternate analytical technique, a calibration can be calculated.

Figure 21:
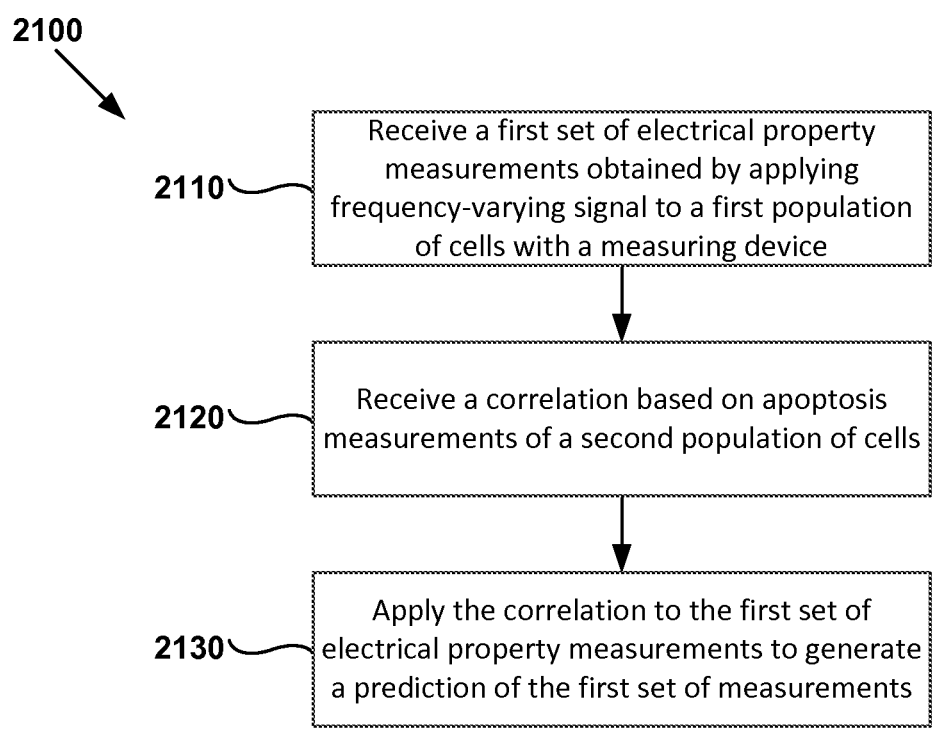
FIG. 21 is a flow chart that illustrates a generalized example of a method of applying a correlation based on an alternate analytical method to generate a prediction using a number of permittivity measurements.

Example Method of Correlating Permittivity Measurements to Alternate Calibration Measurements FIG. 21 is a flow chart 2100 that outlines an exemplary method of applying a correlation of permittivity measurements obtained at varying frequencies to measurements of a biological property obtained using an an alternate analytical technique, as can be used in certain embodiments of the disclosed technology.

At process block 2110, a number of permittivity measurements are received that are obtained by applying a frequency-varying signal to a population of cells using a suitable measuring device, as previously described. Suitable frequencies and techniques for applying a frequency-varying signal to a population of cells as described above regarding process block 2110 can be employed.

The permittivity measurements across all frequency spectra can be normalized to a range from 0.0 to 1.0. After obtaining a number of permittivity measurements and (optionally) normalizing the permittivity measurements, the method proceeds to process block 2120.

At process block 2120, a correlation is received that has been calculated between the permittivity measurements obtained at process block 2110 and calibration measurements determined using an alternate analytical technique in a similar fashion to those described above, e.g., regarding process blocks 760 or 1420. After the divergence has been calculated, the method proceeds to process block 2130.

At process block 2130, the correlation received at process block 2120 is applied to generate a prediction of apoptosis in the first population of cells. In some examples, a first area $a_1$ is determined by integrating a number of permittivity measurements (or samples) taken between a selected low frequency $f_L$ and a selected high frequency $f_H$. In some examples, the highest and lowest frequencies are the highest and lowest frequencies applied to the population of cells when measuring permittivities. In other examples, other high and low frequencies are used as the selected frequencies. In some examples, the permittivity measurements are normalized, as discussed above regarding process block 2110. The first area $a_1$ can be calculated using any suitable technique, including quadrature polynomial interpolation, adaptive quadrature interpolation, extrapolation, and/or Monte Carlo analysis.

FIGS. 19E and 19F are graphs 1960 and 1980 that illustrate relationships between the correlation received and an area ratio, as described above regarding process block 2130. As shown in FIG. 19E, a control cell population exhibits a relatively stable area ratio 1970 over time. As shown in FIG. 19F, an apoptosis-induced cell population exhibits an increase in area ratio 1975 after an apoptosis-inducing agent is added at time 1990. Based on these observations, the change in the beta dispersion curve can be correlated and used to predict cell viability due to apoptosis in the first set of measurements obtained at process block 2110.

Figure 22A:
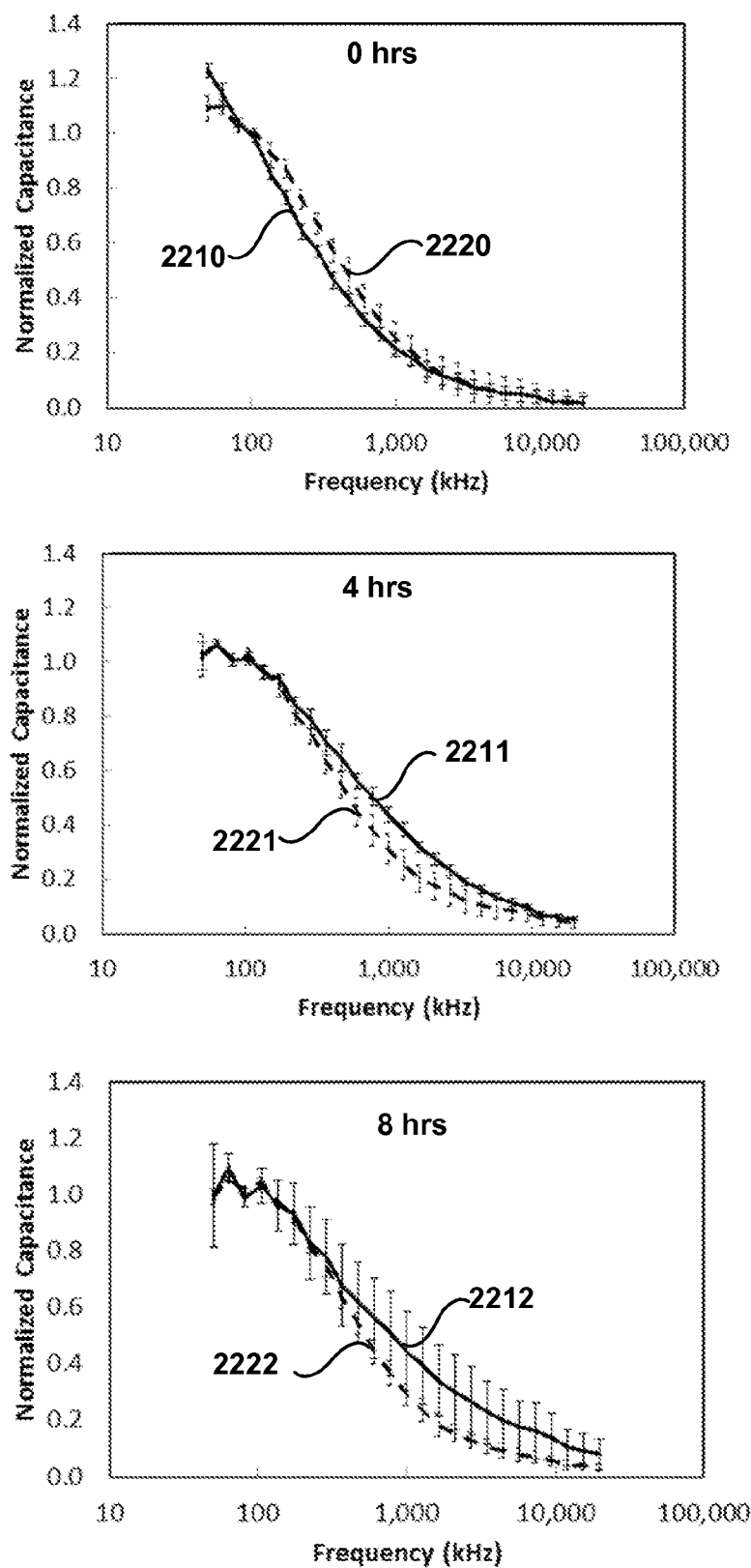

FIGS. 22A-C is a series of charts illustrating changes in dielectric spectra for two cell populations over a 28-hour period. Data series for the first cell population, which has had apoptosis induced using staurosporine induction, are indicated by solid lines (e.g., lines 2210-2216). Data series for the second, control cell population, which has not had apoptosis induced, are indicated by dashed lines (e.g., lines 2220-2226).

A number of different analytical methods can be used to observe cell viability. For example, viable cell volume (VCV), measured using an automated cell counter (e.g., a Cedex analyzer), can be used to automatically count cells to determine VCV using trypan blue exclusion. In some examples, a cell staining technique (e.g., having a DNA, caspase 3, caspase 6, caspase 9, or phosphatidyl-serine stain target) can be employed. As will be readily understood to one of ordinary skill in the art, any of a number of suitable alternate analytical techniques can be used. Further, the calibration measurements are not limited to VCV, but in some examples can include other biomass properties such as packed viable cell volume (PVCV), viable cell density (VCD), viable cell concentration (VCC), viability, cell health, level of apoptosis, or other suitable measurements. The correlation can be calculated using a suitable technique, including linear correlation methods (e.g., using Pearson's linear correlation), non-linear correlation (e.g., using Spearman's rank correlation), or matrix correlation techniques. Thus, in some examples, a correlation in slope-intercept form is calculated, while in other examples, more complex correlations are used. The correlations thus calculated can be used to correct for divergences observed in other cell cultures using permittivity measurements, or measurements of other suitable electrical properties.

Example Computing Environment

Figure 23:
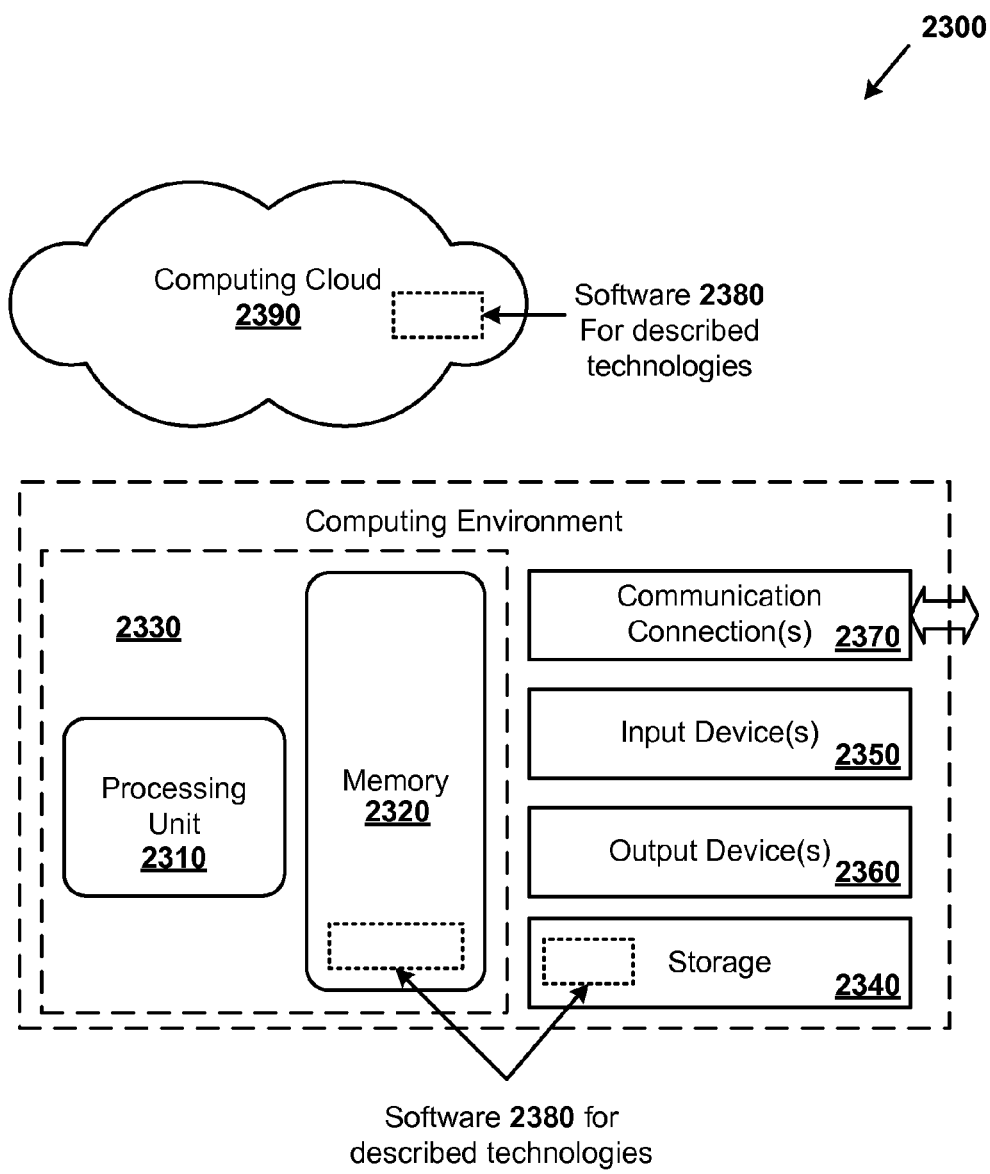
FIG. 23 illustrates a generalized example of a suitable computing environment in which described embodiments, techniques, and technologies can be implemented.

FIG. 23 illustrates a generalized example of a suitable computing environment 2300 in which described embodiments, techniques, and technologies can be implemented. For example, the computing environment 2300 can be used to generate correlations and predict viable cell volumes, as described above.

The computing environment 2300 is not intended to suggest any limitation as to scope of use or functionality of the technology, as the technology can be implemented in diverse general-purpose or special-purpose computing environments. For example, the disclosed technology can be implemented with other computer system configurations, including hand held devices, multiprocessor systems, microprocessor-based or programmable consumer electronics, network PCs, minicomputers, mainframe computers, and the like. The disclosed technology can also be practiced in distributed computing environments where tasks are performed by remote processing devices that are linked through a communications network. In a distributed computing environment, program modules can be located in both local and remote memory storage devices.

With reference to FIG. 23, the computing environment 2300 includes at least one central processing unit 2310 and memory 2320. In FIG. 23, this most basic configuration 2330 is included within a dashed line. The central processing unit 2310 executes computer-executable instructions and can be a real or a virtual processor. In a multi-processing system, multiple processing units execute computer-executable instructions to increase processing power and as such, multiple processors can be running simultaneously. The memory 2320 can be volatile memory (e.g., registers, cache, RAM), non-volatile memory (e.g., ROM, EEPROM, flash memory, etc.), or some combination of the two. The memory 2320 stores software 2380 that can, for example, implement the technologies described herein. A computing environment can have additional features. For example, the computing environment 2300 includes storage 2340, one or more input devices 2350, one or more output devices 2360, and one or more communication connections 2370. An interconnection mechanism (not shown) such as a bus, a controller, or a network, interconnects the components of the computing environment 2300. Typically, operating system software (not shown) provides an operating environment for other software executing in the computing environment 2300, and coordinates activities of the components of the computing environment 2300.

The storage 2340 can be removable or non-removable, and includes magnetic disks, magnetic tapes or cassettes, CD-ROMs, CD-RWs, DVDs, or any other medium which can be used to store information and that can be accessed within the computing environment 2300. The storage 2340 stores instructions for the software 2380 and data (e.g., measurement data or correlation data), which can be used to implement technologies described herein.

The input device(s) 2350 can be a touch input device, such as a keyboard, keypad, mouse, touch screen display, pen, or trackball, a voice input device, a scanning device, or another device, that provides input to the computing environment 2300. For audio, the input device(s) 2350 can be a sound card or similar device that accepts audio input in analog or digital form, or a CD-ROM reader that provides audio samples to the computing environment 2300. The output device(s) 2360 can be a display, printer, speaker, CD-writer, or another device that provides output from the computing environment 2300.

The communication connection(s) 2370 enable communication over a communication medium (e.g., a connecting network) to another computing entity. The communication medium conveys information such as computer-executable instructions, compressed graphics information, video, or other data in a modulated data signal.

The input device(s) 2350, output device(s) 2360, and communication connection(s) 2370 can be used with a control system to control inputs and/or outputs for a bioreactor. For example, input devices can be used with a control system for modulating feeding media, water, acid/base solutions, heat, and agitation for an aseptic bioreactor. Further, output devices can be used with a control system for sampling or removing cells or fluid from a cell population on a bioreactor or to operate a flow cytometer. In some examples, a communication connection 2370, such as an RS-232, USB, Ethernet, or other suitable connection, is used to control bioreactor operation and to adjust environmental conditions.

Some embodiments of the disclosed methods can be performed using computer-executable instructions implementing all or a portion of the disclosed technology in a computing cloud 2390. For example, generating correlations and predicting cell viability can be performed on servers located in the computing cloud 2390.

Computer-readable media are any available media that can be accessed within a computing environment 2300. By way of example, and not limitation, with the computing environment 2300, computer-readable media include memory 2320 and/or storage 2340. As should be readily understood, the term computer-readable storage media includes the media for data storage such as memory 2320 and storage 2340, and not transmission media carrying modulated data signals or transitory signals.

Any of the methods described herein can be performed via one or more computer-readable media (e.g., storage or other tangible media) comprising (e.g., having or storing) computer-executable instructions for performing (e.g., causing a computing device to perform) such methods. Operation can be fully automatic, semi-automatic, or involve manual intervention.

Having described and illustrated the principles of our innovations in the detailed description and accompanying drawings, it will be recognized that the various embodiments can be modified in arrangement and detail without departing from such principles. It should be understood that the programs, processes, or methods described herein are not related or limited to any particular type of computing environment, unless indicated otherwise. Various types of general purpose or specialized computing environments can be used with or perform operations in accordance with the teachings described herein. Elements of embodiments shown in software can be implemented in hardware and vice versa.

In some embodiments of the disclosed technology, methods include receiving a plurality of measurements of at least one electrical property of a population of cells, the measurements having been obtained by applying a frequency-varying signal to the population with a measuring device, and calculating a divergence between the plurality of measurements and a plurality of calibration measurements, the calibration measurements having been obtained using an alternate analytical technique.

In some examples of these methods, the plurality of measurements are obtained over a plurality of different times in a time period, and the divergence is calculated over the time period. In some examples, the electrical property can include at least one or more of the following: capacitance, permittivity, dielectric constant, resistance, impedance, voltage, or current. In some examples, the measurements are made using a permittivity probe.

Some examples these methods include normalizing the measurements by the electrical property measured at a selected frequency ($f_Q$) of the first frequency-varying signal. In some examples, the divergence is calculated by determining a first area ($a_1$) by calculating an integral of the electrical property between a low frequency ($f_L$) of the first frequency-varying signal and a high frequency ($f_H$) of the frequency-varying signal, determining a second area ($a_2$) by calculating an integral of the electrical property between the selected frequency ($f_Q$) and the high frequency ($f_H$) or between the selected frequency ($f_Q$) and the low frequency ($f_L$), the selected frequency ($f_Q$) being greater than the low frequency ($f_L$) and less than the high frequency ($f_H$), generating an area ratio based on the first area ($a_1$) and the second area ($a_2$), and correlating the area ratio with the calibration measurements determined using the alternate analytical method. In some examples of normalizing the measurements, the low frequency ($f_L$) is the lowest frequency of the frequency-varying signal and the high frequency ($f_H$) is the highest frequency of the frequency-varying signal. In some examples of the method above, the measurements include at least one or more of the following: viable cell volume (VCV), packed viable cell volume (PVCV), viable cell density (VCD), viable cell concentration (VCC), viability, or cell health.

In some embodiments of the disclosed technology, methods include receiving a first plurality of measurements of at least one electrical property of a first population of cells, the measurements obtained by applying a first frequency-varying signal to a first population of cells with a measuring device, receiving a correlation based on a second plurality of measurements of at least one electrical property of a second population of cells, and applying the correlation to the first plurality of measurements to generate a prediction of the first plurality of measurements for the first population of cells.

In some examples of these methods, the plurality of measurements are obtained over a plurality of different times in a time period, and the correlation is applied over the time period. In some examples, the correlation is based on divergences between the second plurality of measurements and at least one calibration measurement, the calibration measurement determined using an alternate analytical method. In some examples, the electrical property includes at least one or more of the following: capacitance, permittivity, dielectric constant, resistance, impedance, voltage, or current. In some examples, the first measurements are made using a permittivity probe. In some examples, the method further comprises normalizing the first measurements by the electrical property measured at a selected frequency ($f_Q$) of the first frequency-varying signal.

In some examples, the second plurality of measurements is obtained by applying a second frequency-varying signal to the second population of cells, and the correlation is calculated by: determining a first area ($a_1$) by calculating an integral of the electrical property between a low frequency ($f_L$) of the first frequency-varying signal and a high frequency ($f_H$) of the second frequency-varying signal, determining a second area ($a_2$) by calculating an integral of the electrical property between the selected frequency ($f_Q$) and the high frequency ($f_H$) or between the selected frequency ($f_Q$) and the low frequency ($f_L$), the selected frequency ($f_Q$) being greater than the low frequency ($f_L$) and less than the high frequency ($f_H$), generating an area ratio based on the first area ($a_1$) and the second area ($a_2$), and correlating the area ratio with the calibration measurements determined using the alternate analytical method.

In some examples of these methods, the electrical property includes permittivity, and the applying the correlation comprises normalizing the first measurements by a permittivity measured at a selected frequency of the first frequency-varying signal. In some examples, the selected frequency of the first frequency-varying signal is the same selected frequency of the second frequency-varying signal.

In some examples of these methods, applying a correlation comprises normalizing the measurements according to the following equation:

$$\varepsilon_N = \frac{\varepsilon}{\varepsilon_{max}}$$

where $\varepsilon_N$ is the normalized measurement, $\varepsilon$ is one of the measurements, and $\varepsilon_{max}$ is a maximum measurement of the first plurality of measurements.

In some examples, applying the correlation comprises calculating area ratios based on at least one of the following equations:

$$R_A = \frac{\int_{f_Q}^{f_H} \varepsilon(f) df}{\int_{f_L}^{f_H} \varepsilon(f) df} \text{ or } R_A = \frac{\int_{f_L}^{f_Q} \varepsilon(f) df}{\int_{f_L}^{f_H} \varepsilon(f) df}$$

where $R_A$ is the calculated area ratio, $\varepsilon(f)$ corresponds to the electrical property obtained by applying the first frequency-varying signal to the first population of cells, and $f_Q$ is the selected frequency of the first frequency-varying signal within a range between the low frequency $f_L$ and the high frequency $f_H$.

In some examples, these methods further includes adjusting one or more environmental conditions for the first population of cells based on the prediction. The environmental conditions can include at least one or more of the following: feed rate, temperature, agitation rate, atmospheric conditions, pH, or lighting conditions.

Some examples of these methods further include calculating a correlation by: receiving the second plurality of measurements of at least one electrical property of the second population of cells, the second plurality of measurements obtained by applying a second frequency-varying signal to the second population of cells with a measuring device, and calculating the correlation based on a divergence between the plurality of measurements and at least one calibration measurement, the calibration measurement determined using an alternate analytical method.

In some examples, the alternate analytical method is one of a hemocytometer, trypan blue exclusion, caspases for measuring cell apoptosis, fluorescence-activated cell sorting using flow cytometry, or combinations thereof. Some examples of the method above include adjusting one or more environmental conditions for the first population of cells based on the prediction to produce a bioproduct comprising at least a portion of the first population of cells.

In some embodiments of the disclosed technology, apparatus are configured to perform one or more of the preceding methods. In some examples, an apparatus includes a reactor for growing cells in a population contained in the reactor, a permittivity measuring device coupled to the reactor, the permittivity measuring device being configured to apply a frequency-varying electrical signal to the population to measure at least one electrical property of the population, processing resources coupled to the permittivity measuring device, and computer-readable storage media storing computer-readable instructions that when executed by the processing resources cause the apparatus to perform the method of one or more of the exemplary methods disclosed herein.

In some embodiments of the disclosed technology, methods include receiving a first set of data based on measurements for a first population of cells, the measurements having been obtained using a first analytical method, receiving a second set of data based on measurements for a second population of cells, the measurements for the second set of data having been obtained by applying an electrical signal having two or more different frequencies to the second population of cells, generating a correlation between the first set of data and the second set of data, and correcting measurements for the second population of cells based on the correlation.

In some embodiments, these methods include obtaining a plurality of permittivity measurements for a population of cells by applying a frequency-varying signal to the population with a permittivity device, determining a first area by calculating an integral of the permittivity measurements between a low frequency of the frequency-varying signal and a high frequency of the frequency-varying signal, determining a second area by calculating an integral of the permittivity measurements between a selected frequency and the high frequency or between the selected frequency and the low frequency, the selected frequency being greater than the low frequency and less than the higher frequency, generating an area ratio based on the first area and the second area, and generating a prediction of a viable cell volume for the population based on a correlation between the area ratio and a second prediction of viable cell volume, the second prediction of viable cell volume determined using trypan blue exclusion.

In some examples, these methods further include determining the correlation by correlating area ratios for a second frequency-varying signal applied to a second population of cells with a permittivity device and predictions of viable cell volume predictions determined using trypan blue exclusion. In some examples, the low frequency is the lowest frequency applied to the population using the frequency-varying varying signal and the high frequency is the highest frequency applied to the population using the frequency-varying signal.

In some examples of these methods, the population is a first population, and the methods further include obtaining a plurality of permittivity measurements for a second population of cells by applying a second frequency-varying signal to the second population with a permittivity device, determining area ratios for the second population of cells between (1) a respective first area between a low and high frequency of the second frequency-varying signal and (2) a respective second area between a selected frequency and the low or the high frequency of the second frequency-varying signal, determining viable cell volumes for the second population using trypan blue exclusion to produce second predicted viable cell volumes, and determining a correlation function for area ratios for the second population of cells and the second predicted viable cell volumes, and wherein the generating the prediction of the viable cell volume for the first population is based on the correlation function.

Some examples of the methods above further include adjusting a feeding scheme for the population of cells based on the predicted viable cell volume. Some examples include adjusting one or more environmental conditions for the population of cells based on the predicted viable cell volume.

In some embodiments of the disclosed technology, methods include growing cells in a conductive medium, receiving a prediction of the viability of the cells, the prediction having been determined based on a correlation between a predicted viability determined using a first measurement technique and measurements determined using a second measurement technique, the second technique comprising applying a frequency-varying signal to the conductive medium, and based on the viability prediction, adjusting the conditions of the conductive medium.

In some examples, the cells include mammalian cells. In some examples of these methods, the adjusting comprises adjusting at least one or more of the following: feed rate, temperature, agitation rate, atmospheric conditions, pH, or lighting conditions. In some examples, the measurements and/or conditions are determined before a peak in the predicted viability of the cells. In some examples the measurements and/or conditions are determined after a peak in the predicted viability of the cells.

In some embodiments of the disclosed technology, an apparatus includes a reactor for growing cells in a conductive medium, a measuring device coupled to the reactor, the measuring device being operable to apply a frequency-varying electrical signal to a conductive medium to measure electrical properties of the population, and processing resources coupled to the measuring device operable to determine a predicted viability of the cells in the conductive medium according to one or more of the methods above.

In some examples, an apparatus includes a reactor for growing cells in a conductive medium, one or more adjustable inputs to the reactor, a measuring device coupled to the reactor, the measuring device being operable to apply a frequency-varying electrical signal to the conductive medium to measure electrical properties of the conductive medium, and processing resources coupled to the measuring device, the processing resources being operable to determine a predicted viability of the cells in the conductive medium according to one or more of these methods, the processing resources being operable to adjust the conditions of the conductive medium by adjusting the inputs to the reactor.

In some examples of the disclosed technology, methods include receiving a first set of measurements of at least one electrical property of a first population of cells, the first set of measurements having been obtained by applying a frequency-varying signal to the first population with a measuring device, receiving a second set of measurements of at least one electrical property of a second population of cells, the second set of measurements having been obtained by applying a frequency-varying signal to the second population with a measuring device, where one or more environmental parameters of the second population of cells are changed in comparison to the first population of cells, comparing the first set of measurements to the second set of measurements and, based on the comparing, predicting apoptosis in the first population or the second population.

In some examples of these methods, first and second sets of measurements are obtained over a plurality of different times in a time period, and the comparing is performed over the time period.

In some examples of these methods, an electrical property includes at least one or more of the following: capacitance, permittivity, dielectric constant, resistance, impedance, voltage, or current. In some examples, the first set of measurements and the second set of measurements are made using a permittivity probe. Some examples further include adjusting the environmental parameters of the second population of cells. Some examples further include treating the second population of cells with staurosporine at one or more time periods.

Some examples of these methods include measuring apoptosis by staining a sample of the first population of cells with at least one staining agent, a sample of the second population of cells, or a sample of the first population of cells and a sample of the second population of cells to detect a stain target, wherein the predicting is based at least in part on the measured apoptosis.

In some examples the stain target detected with the staining agent includes at least one or more of the following: DNA, caspase 3, caspase 6, caspase 9, or phophatidylserine. In some examples, measuring apoptosis by staining includes adjusting at least one or more of the following parameters: an amount of the staining agent used, a time duration of exposure to a staining agent, or a wash of a staining agent.

Some examples of these methods include normalizing the first set of measurements and the second set of measurements by the electrical property measured at a selected frequency ($f_Q$) of the first frequency-varying signal.

In some examples, the act of comparing includes determining a first area ($a_1$) by calculating an integral of the electrical property between a low frequency ($f_L$) of the first frequency-varying signal and a high frequency ($f_H$) of the frequency-varying signal, determining a second area ($a_2$) by calculating an integral of the electrical property between the selected frequency ($f_Q$) and the high frequency ($f_H$) or between the selected frequency ($f_Q$) and the low frequency ($f_L$), the selected frequency ($f_Q$) being greater than the low frequency ($f_L$) and less than the high frequency ($f_H$), generating an area ratio based on the first area ($a_1$) and the second area ($a_2$), and correlating the area ratio with the calibration measurements determined using the alternate analytical method. In some examples, the low frequency ($f_L$) is the lowest frequency of the frequency-varying signal and the high frequency ($f_H$) is the highest frequency of the frequency-varying signal.

In some examples, the first set of measurements and the second set of measurements include at least one or more of the following: viable cell volume (VCV), packed viable cell volume (PVCV), viable cell density (VCD), viable cell concentration (VCC), viability, cell viability percentage, or cell health.

In some embodiments of the disclosed technology, methods include receiving a first plurality of measurements of at least one electrical property of a first population of cells, the measurements obtained by applying a first frequency-varying signal to a first population of cells with a measuring device, receiving a correlation based on a second plurality of measurements of at least one electrical property of a second population of cells, the correlation based at least in part on one or more measurements of apoptosis in the second population of cells, and applying the correlation to the first plurality of measurements to generate a prediction of apoptosis for the first population of cells.

In some examples of these methods, a plurality of measurements are obtained over a plurality of different times in a time period, and the correlation is applied over the time period. In some examples, the measurements of apoptosis are determined using a staining technique on the second population of cells.

In some examples, the electrical property includes at least one or more of the following: capacitance, permittivity, dielectric constant, resistance, impedance, voltage, or current. In some examples, the first measurements are made using a permittivity probe.

Some examples of the methods above include normalizing the measurements by the electrical property measured at a selected frequency ($f_Q$) of the first frequency-varying signal.

In some examples of the method above, the electrical property includes permittivity, and the applying the correlation comprises normalizing the first measurements by a permittivity measured at a selected frequency of the first frequency-varying signal. In some examples, the selected frequency of the first frequency-varying signal is the same selected frequency of the second frequency-varying signal.

Some examples of the method above further include adjusting one or more environmental conditions for the first population of cells based on the prediction. In some examples, the environmental conditions include at least one or more of the following: feed rate, temperature, agitation rate, atmospheric conditions, pH, or lighting conditions. In some examples, the alternate analytical method is one of a hemocytometer, trypan blue exclusion, caspases for measuring cell apoptosis, fluorescence-activated cell sorting using flow cytometry, or combinations thereof.

In some embodiments, an apparatus includes a reactor for growing cells in a population contained in the reactor, a permittivity measuring device coupled to the reactor, the permittivity measuring device being configured to apply a frequency-varying electrical signal to the population to measure at least one electrical property of the population, one or more processing resources coupled to the permittivity measuring device, and computer-readable storage media storing computer-readable instructions that when executed by the processing resources cause the apparatus to perform one or more of the methods disclosed herein.

In some embodiments, methods include growing cells in a conductive medium, receiving a prediction of the viability of the cells, the prediction having been determined based on a correlation between a predicted apoptosis level determined using a first measurement technique and measurements determined using a second measurement technique, the second technique comprising applying a frequency-varying signal to the conductive medium, and based on the viability prediction, adjusting the conditions of the conductive medium.

In some examples of these methods, the cells include mammalian cells. In some examples, the adjusting comprises adjusting at least one or more of the following: feed rate, temperature, agitation rate, atmospheric conditions, pH, or lighting conditions.

In some examples of these methods, the measurements are determined before and/or after a peak in the predicted viability of the cells. In some examples, the conditions are adjusted before and/or after a peak in the predicted viability of the cells.

In some embodiments of the disclosed technology, an apparatus includes a reactor for growing cells in a conductive medium, a measuring device coupled to the reactor, the measuring device being operable to apply a frequency-varying electrical signal to a conductive medium to measure electrical properties of the population, and processing resources coupled to the measuring device, the processing resources being operable to determine a predicted viability of the cells in the conductive medium according to one or more of the methods disclosed herein.

In some embodiments, an apparatus includes a reactor for growing cells in a conductive medium, one or more adjustable inputs to the reactor, a measuring device coupled to the reactor, the measuring device being operable to apply a frequency-varying electrical signal to the conductive medium to measure electrical properties of the conductive medium, and processing resources coupled to the measuring device, the processing resources being operable to determine a predicted viability of the cells in the conductive medium according to one or more of the methods disclosed herein, the processing resources being operable to adjust the conditions of the conductive medium by adjusting the inputs to the reactor.

In some examples, the methods disclosed herein include producing a bioproduct.

In some examples, computer-readable storage media store computer-readable instructions that when executed by a computer, cause the computer to perform one or more of the methods disclosed herein.

In view of the many possible embodiments to which the principles of the disclosed invention may be applied, it should be recognized that the illustrated embodiments and their equivalents are only preferred examples of the invention and should not be taken as limiting the scope of the invention.

We claim:

1. A method for determining a biological property of cells suspended in a liquid media, the method comprising:
    applying an electrical signal to said cells suspended in said liquid media at two or more signal frequencies to generate electrical property data;
    receiving biological property data obtained using an alternate analytical technique;
    generating at least one value representative of frequency dependence of said electrical property data;
    determining a first relationship between said biological property data and said electrical property data;
    determining a second relationship between (1) said value representative of the frequency dependence of said electrical property data and (2) a divergence between a magnitude of said biological property data and a magnitude of said electrical property data;
    determining a calibration function by combining said first relationship and said second relationship;
    by a computer, calculating said calibration function with subsequent electrical property data to determine said biological property of said cells; and
    adjusting one or more environmental conditions of said liquid media in response to determining said biological property of said cells.

2. The method of claim 1, wherein said value representative of the frequency dependence of said electrical property data represents a shape of said electrical property data relative to frequency.

3. The method of claim 1, wherein said electrical property data are obtained at two or more time points, and said value representative of the frequency dependence of said electrical property data is generated at each respective time point.

4. The method of claim 1, wherein said value representative of the frequency dependence of said electrical property data is generated by calculating a ratio from said electrical property data collected at different frequencies.

5. The method of claim 1, wherein said value representative of the frequency dependence of said electrical property data is generated by:
    determining a first area ($a_1$) by calculating an integral of said electrical property data between a low frequency ($f_L$) of said electrical signal and a high frequency ($f_H$) of said electrical signal;
    determining a second area ($a_2$) by calculating an integral of said electrical property data between a selected frequency ($f_Q$) and said high frequency ($f_H$) or between said selected frequency ($f_Q$) and said low frequency ($f_L$), said selected frequency ($f_Q$) being greater than said low frequency ($f_L$) and less than said high frequency ($f_H$); and
    calculating an area ratio based on said first area ($a_1$) and said second area ($a_2$).

6. The method of claim 5, wherein the low frequency ($f_L$) is substantially the lowest frequency of said two or more signal frequencies and the high frequency ($f_H$) is substantially the highest frequency of said two or more signal frequencies.

7. The method of claim 1, wherein said determining said second relationship comprises applying a correlation between said divergence and said value representative of the frequency dependence of said electrical property data.

8. The method of claim 1, wherein said value representative of the frequency dependence of said electrical property data is representative of both a magnitude and the frequency-dependence of said electrical property data.

9. The method of claim 1 wherein said electrical property data includes at least one or more of the following: capacitance, permittivity, dielectric constant, resistance, impedance, voltage, or current.

10. The method of claim 1, wherein said biological property data includes at least one or more of the following: viable cell volume (VCV), packed viable cell volume (PVCV), viable cell density (VCD), viable cell concentration (VCC), viability, cell health, or a level of apoptosis.

11. The method of claim 1, wherein:
    said electrical property data includes permittivity measurements; and
    said method further comprises applying said calibration function to said subsequent electrical property data to generate a prediction of apoptosis for said cells, said applying comprising normalizing said permittivity measurements by a permittivity measured at a selected frequency of said two or more signal frequencies.

12. The method of claim 11, wherein:
said applying said calibration function comprises normalizing said permittivity measurements according to the following equation:

$$\varepsilon_N = \frac{\varepsilon}{\varepsilon_{max}}$$

wherein $\varepsilon_N$ is the normalized measurement, $\varepsilon$ is one of said permittivity measurements, and $\varepsilon_{max}$ is a maximum measurement of said permittivity measurements.

13. The method of claim 11, wherein said applying said calibration function comprises calculating area ratios based on at least one of the following equations:

$$R_A = \frac{\int_{f_Q}^{f_H} \varepsilon(f)\,df}{\int_{f_L}^{f_H} \varepsilon(f)\,df} \text{ or } R_A = \frac{\int_{f_L}^{f_Q} \varepsilon(f)\,df}{\int_{f_L}^{f_H} \varepsilon(f)\,df}$$

wherein $R_A$ is the calculated area ratio, $\varepsilon(f)$ corresponds to said electrical property obtained by applying said electrical signal to said cells, $f_Q$ is said selected frequency of said frequency-varying signal within a range between said low frequency $f_L$ and said high frequency $f_H$, $f_L$ is substantially the lowest frequency of said two or more signal frequencies, $f_H$ is substantially the highest frequency of said two or more signal frequencies, and df is the differential of f.

14. The method of claim 1, wherein:
said biological property data comprises first biological property data and second biological property data;
said first biological property data comprises at least one or more of the following: viable cell volume (VCV), packed viable cell volume (PVCV), viable cell density (VCD), or viable cell concentration (VCC); and
said second biological property data comprises viability, cell health, or viability and cell health.

15. The method of claim 1, wherein said determining said second relationship is further based on a shape of a frequency-dependent curve between said divergence and said value representative of frequency dependence of said electrical property data.

16. One or more computer-readable storage media storing computer-readable instructions that when executed by a computer, cause the computer to perform a method, the method comprising:
generating electrical property data by causing an electrical measuring device to apply a signal to a liquid suspension of cells at two or more signal frequencies at multiple time points;
receiving biological property data obtained using an alternate analytical technique;
generating at least one value representative of a shape representing frequency dependence of said electrical property data;
quantifying at each of said multiple time points a magnitude of divergence between said biological property data and said electrical property data;
determining a relationship between said magnitude of divergence and said value representative of the shape representing frequency dependence of said electrical property data;
determining a calibration function based on said relationship;
by a computer, calculating said calibration function with subsequent electrical property data to determine said biological property of said cells; and
by the computer, generating an output signal, the output signal controlling one or more input and/or output devices effecting a measurement or alteration in environmental conditions within a vessel containing at least a portion of said cells.

17. A method for determining a biological property of cells suspended in a liquid media in a bioreactor, the method comprising:
receiving electrical property data obtained by applying a signal to said cells at two or more signal frequencies at multiple time points;
receiving biological property data obtained using an alternate analytical technique;
generating at least one value representative of frequency dependence of said electrical property data;
quantifying at each of said multiple time points a magnitude of divergence between said biological property data and said electrical property data;
determining a relationship between said magnitude of divergence and said value representative of frequency dependence of said electrical property data between each of said multiple time points;
generating a calibration function based on said relationship;
repeatedly applying said calibration function to subsequent electrical property data to determine said biological property of said cells; and
adjusting one or more environmental conditions of said bioreactor in response to determining said biological property of said cells.

18. The method of claim 17, further comprising generating the received electrical property data by applying said signal to the cells suspended in the liquid media in the bioreactor at the two or more signal frequencies.

* * * * *